(12) United States Patent
Tulchinsky et al.

(10) Patent No.: US 8,466,306 B2
(45) Date of Patent: Jun. 18, 2013

(54) SULFONATED ORGANOPHOSPHINE COMPOUNDS AND USE IN HYDROFORMYLATION PROCESSES

(75) Inventors: Michael L. Tulchinsky, Midland, MI (US); Ronald R. Peterson, St. Albans, WV (US)

(73) Assignee: Dow Global Technologies LLC, Midland, MI (US)

( * ) Notice: Subject to any disclaimer, the term of this patent is extended or adjusted under 35 U.S.C. 154(b) by 133 days.

(21) Appl. No.: 12/812,978

(22) PCT Filed: Jan. 9, 2009

(86) PCT No.: PCT/US2009/030553
§ 371 (c)(1),
(2), (4) Date: Aug. 25, 2010

(87) PCT Pub. No.: WO2009/091669
PCT Pub. Date: Jul. 23, 2009

(65) Prior Publication Data
US 2011/0054203 A1    Mar. 3, 2011

Related U.S. Application Data

(60) Provisional application No. 61/021,065, filed on Jan. 15, 2008.

(51) Int. Cl.
*C07F 9/02*    (2006.01)

(52) U.S. Cl.
USPC .............................. 556/21; 568/420; 568/454

(58) Field of Classification Search
USPC ...................................... 556/21; 568/420, 454
See application file for complete search history.

(56) References Cited

U.S. PATENT DOCUMENTS

| | | |
|---|---|---|
| 2,900,393 A | 8/1959 | Broderick |
| 3,527,809 A | 9/1970 | Pruett et al. |
| 4,148,830 A | 4/1979 | Pruett et al. |
| 4,247,486 A | 1/1981 | Brewester et al. |
| 4,283,304 A | 8/1981 | Bryant et al. |
| 4,483,802 A | 11/1984 | Gartner et al. |
| 4,625,068 A | 11/1986 | Young |
| 4,642,388 A | 2/1987 | Young |
| 4,689,437 A | 8/1987 | Murray |
| 4,716,138 A | 12/1987 | Murray |
| 4,731,486 A | 3/1988 | Abatjoglou et al. |
| 4,822,915 A | 4/1989 | Murray |
| 5,180,854 A | 1/1993 | Abatjoglou et al. |
| 5,382,701 A | 1/1995 | Suciu et al. |
| 5,451,698 A | 9/1995 | Bahrmann et al. |
| 5,663,426 A | 9/1997 | Albanese et al. |
| 5,728,886 A | 3/1998 | Naumann et al. |
| 5,760,286 A | 6/1998 | Brandvold |
| 5,773,666 A | 6/1998 | Omatsu et al. |
| 5,780,674 A | 7/1998 | Albanese et al. |
| 5,925,785 A | 7/1999 | Stelzer et al. |
| 5,929,289 A | 7/1999 | Abatjoglou et al. |
| 5,932,772 A | 8/1999 | Argyropoulos et al. |
| 5,952,530 A | 9/1999 | Argyropoulos et al. |
| 6,103,908 A | 8/2000 | Bahrmann et al. |
| 6,339,174 B1 | 1/2002 | Bogdanovic |
| 6,610,881 B1 | 8/2003 | Riedel et al. |
| 6,613,939 B2 | 9/2003 | Aouni et al. |
| 6,864,387 B2 | 3/2005 | Riedel et al. |
| 2003/0204109 A1 | 10/2003 | Aouni et al. |
| 2009/0253907 A1* | 10/2009 | Plenio et al. .................. 544/163 |

FOREIGN PATENT DOCUMENTS

| | | |
|---|---|---|
| EP | 0350921 A1 | 1/1990 |
| EP | 1620387 A2 | 2/2006 |
| WO | WO-2004/094440 A2 | 11/2004 |
| WO | WO-2004/096744 | 11/2004 |
| WO | WO-2007035540 A2 | 3/2007 |

OTHER PUBLICATIONS

Ashby, E. et al. "Single electron transfer in the reaction of enolates with alkyl halides," J.Org.Chem. (1985) 50:3274-3283.*
Abatjoglou et al, Organometallics, 1984, p. 923-926, vol. 3, American Chemical Society.
Arvidsson et al, Canadian Journal of Chemstry, 1998, p. 795-799, vol. 76, Canada.
Ashby, Journal of Organic Chemistry,1985, p. 3274-3283, vol. 50, American Chemical Society.

(Continued)

*Primary Examiner* — Johann R Richter
*Assistant Examiner* — Pancham Bakshi

(57) ABSTRACT

A compound comprising a sulfonated dihydrocarbyl(aryalkyl)phosphine of formula $R^1R^2PR^3$—$(SO_3M)_n$, wherein the $R^1$ and $R^2$ are selected individually from alkyl, aralkyl, and alicyclic groups, and $R^3$ is a divalent or polyvalent arylalkylene radical such that the alkyl moiety is bonded to the phosphorus atom and the aryl moiety is bonded to the alkyl and is also substituted with one or more sulfonate groups; M is a monovalent cation, and n ranges from 1 to 3. The compound is useful as a ligand in transition metal-ligand complex catalysts that are capable of catalyzing the hydroformylation of an olefinically-unsaturated compound with carbon monoxide and hydrogen to form one or more corresponding aldehyde products. The ligand is incapable of alkyl-aryl exchange, thereby leading to reduced ligand usage and improved ligand and transition metal, e.g., rhodium, recovery and recycling.

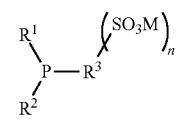

19 Claims, 3 Drawing Sheets

OTHER PUBLICATIONS

Bartik et al, Journal of Molecular Catalysis A: Chemical, 1995, p. 117-122, vol. 98, Elsevier Science BV.
Bartik et al, Organometallics, 1993, p. 164-170, vol. 12, American Chemical Society.
Doppiu et al, European Journal of Inorganic Chemistry, 2004, p. 2244-2252, Wiley-VCH.
Fleckenstein et al, Chemistry—A European Journal, 2007, p. 2701-2716, vol. 13, Wiley-VCH.
Frohning, Applied Homogeneous Catalysis with Organometallic Compounds, 2002, p. 29-103, vol. 1, Wiley-VCH, New York.
Fürstner el al, Chemistry—A European Journal, 2000, p. 1847-1857, vol. 6, Wiley-VCH.
Jane et al, Journal of Organometallic Chemistry, 2000, p. 55-64, vol. 606, Elsevier Science SA.
Kabalka et al, Tosylation of Alcohols, Journal of Organic Chemistry, 1986, p. 2386-2388, vol. 51, American Chemical Society.
Lynn et al, Journal of the American Chemical Society, 2000, p. 6601-6609, vol. 122, American Chemical Society.
Lysenko et al, Journal of Organometallic Chemistry, 2006, p. 5197-5203 vol. 69, Elsevier BV.
McNulty et al, Tetrahedron Letters, 2004, p. 407-409, vol. 45, Elsevier Ltd.
Mohr et al, Organometallics, 1996, p. 4317-4325, vol. 15, American Chemical Society.
Roman Jr. et al, Organometallics, 1997, p. 1484-1490, vol. 16, American Chemical Society.
Tugcu et al, Industrial and Engineering Chemical Research, 2002, p. 6482-6492, vol. 41, American Chemical Society.
Wyatt et al, European Journal of Organic Chemistry, 2003, p. 4216-4226, Wiley-VCH
Yamamoto et al, Chemistry Letters, 1984, p. 1603-1606 ,vol. 7.
Yamamoto et al, Chemistry Letters, 1989, p. 349-352, vol. 1.
PCT/US09/030553 International Search Report.
PCT/US09/030553 Written Opinion of the International Search Authority.
PCT/US09/030553 International Preliminary Report on Patentability.

* cited by examiner

SULFONATED ORGANOPHOSPHINE COMPOUNDS AND USE IN HYDROFORMYLATION PROCESSES

CROSS-REFERENCE TO RELATED APPLICATION

This application claims the benefit of U.S. Provisional Application Ser. No. 61/021,065, filed Jan. 15, 2008.

BACKGROUND OF THE INVENTION

This invention pertains to a novel class of sulfonated organophosphine compounds and their use as ligands in metal-ligand complex catalysts that are capable of catalyzing hydroformylation processes.

Hydroformylation processes are well known in the art, for example, as described in "Applied Homogeneous Catalysis with Organometallic Compounds," edited by B. Cornils and W. A. Herrmann, VCH, New York, 1996, vol. 1, pp. 29-104. Hydroformylation generally involves conversion of an olefinically-unsaturated reactant with carbon monoxide and hydrogen (syngas) to produce one or more corresponding formyl-substituted products (aldehydes). Hydroformylation processes are known to be catalyzed by metal-ligand complex catalysts, preferably, a transition metal-organophosphorus ligand complex catalyst. Representative art disclosing hydroformylation catalysts comprising a variety of triorganophosphine, triorganophosphite, diorganophosphite, and bisphosphite ligands is found in the following general reference "Rhodium Catalyzed Hydroformylation," edited by P. W. N. M. van Leeuwen and C. Clayer, Kluwer Academic Publisher, USA Edition, 2002. If desired, the formyl-substituted products may be subjected to downstream functionalization processes, for example, reduction of the aldehyde to form an alcohol; or reductive amination of the aldehyde to form an amine; or oxidation of the aldehyde to form a carboxylic acid; or aldolization of the aldehyde followed by oxidation to form an hydroxyacid. Alcohols, amines, carboxylic acids, and hydroxyacids obtained via hydroformylation of an olefinically-unsaturated reactant find utility as solvents, surfactants, and monomers for the preparation of polymers, and as intermediates in the synthesis of pharmaceuticals and other industrially-useful chemicals. Preferably, mono-, di-, and tri-alcohols and corresponding amines obtained directly from hydroformylation can be converted via transesterification into polyester polyols and polyester polyamines, respectively, which are especially useful in the manufacture of polyurethane polymers.

The hydroformylation of long-chain olefinically-unsaturated reactants having from 6 to about 60 carbon atoms is of present day interest. In particular, one class of long-chain olefinically-unsaturated reactants comprises a mixture of mono-, di-, and tri-unsaturated fatty acids or fatty acid esters having from about 10 to about 50 carbon atoms, preferably, the olefinically-unsaturated fatty acid esters of lower alkanols, preferably, $C_{1-8}$ mono-alkanols, for example, methanol. Olefinically-unsaturated fatty acid esters of the lower alkanols are themselves derived by transesterifying a seed oil, for example, a soy, castor, or canola vegetable oil, with the $C_{1-8}$ alkanol. Thus, seed oils can provide a renewable alternative feedstock of olefinically-unsaturated fatty acids or fatty esters, which is capable, in part, of replacing petroleum in the manufacture of industrially-useful chemicals.

More specifically, the present day hydroformylation of olefinically-unsaturated fatty acids or fatty esters and other long chain olefinically-unsaturated compounds is conducted in a rhodium-catalyzed one-phase process containing a water-soluble ionic ligand, preferably, an alkali metal salt of a dihydrocarbylarylphosphine monosulfonate compound wherein the hydrocarbyl may comprise an alkyl or aryl group, and further containing a solubilizing solvent, such as N-methyl-2-pyrrolidinone (NMP), as disclosed for example in WO 2004/096744. Separation of the resulting aldehyde-containing reaction product fluid is typically effected via addition of water, as disclosed for example in U.S. Pat. No. 5,180,854, so as to obtain a two-phase system comprising a non-polar phase containing one or more aldehyde products and optionally any non-polar solvent(s) as may be present and a polar phase containing the rhodium-ligand catalyst, optional free ionically-charged ligand, water, and solubilizing solvent. Disadvantageously, ligands containing an aryl-phosphorus bond tend to undergo alkyl-aryl exchange by way of reaction of the phosphine ligand with the olefinically-unsaturated compound, as disclosed in U.S. Pat. No. 4,283,304 and by A. G. Abatjoglou, et al., in *Organometallics*, 1984, 3, 923-926.

Ligand alkyl-aryl exchange generates three undesirable results. First, alkyl-aryl exchange consumes the particular species of ligand active in the hydroformylation process, which then needs to be replaced. Second, alkyl-aryl exchange produces non-ionic or neutral ligands, which are insoluble in water and which can remain along with coordinated rhodium complexes in the non-polar phase containing the aldehyde product(s), rather than being extracted into the polar phase. Third, alkyl-aryl exchange produces sodium benzenesulfonate, which accumulates in the polar phase and can eventually precipitate onto the walls of the reactor equipment and foul the same. Sodium benzenesulfonate may also induce undesirable separation of the water/NMP polar phase.

In view of the above, a search continues to discover novel compounds that can be utilized as ligands in transition metal-ligand complex catalysts for the hydroformylation of olefinically-unsaturated compounds, particularly, unsaturated fatty acids and unsaturated fatty esters and other long-chain olefinically unsaturated compounds. It would be desirable for such novel compounds to provide for comparable or better olefin conversion and product selectivity, as compared with prior art organophosphorus ligands. Moreover, it would be desirable for such novel compounds to provide for improved ligand stability with elimination of alkyl-aryl exchange, as compared with prior art ligands.

U.S. Pat. No. 5,773,666 discloses a hydroformylation process using $P(X_1)(X_2)(X_3—SO_3M)$ as a ligand, wherein $X_1$ and $X_2$ are monovalent hydrocarbon groups with 1-15 carbon atoms, $X_3$ is a divalent hydrocarbon group with 1-15 carbon atoms, and M is an alkali metal. In the description and working examples of U.S. Pat. No. 5,773,666, $X_3$ is disclosed to be specifically 1,3-phenylene or a tri- or tetra-methylene, such that the phenylene or the tri- or tetra-methylene is substituted with a sulfonate group.

U.S. Pat. No. 5,180,854 discloses sulfonated organophosphine ligands of the following generic formula:

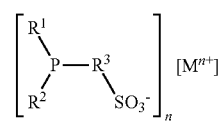

wherein $R^3$ represents a divalent alkylene radical having from 2 to 12 carbon atoms or a divalent 1,3-phenylene radical.

Preferably, when $R^3$ is a divalent alkylene radical, $R^3$ has from 2 to 5 carbon atoms; more preferably, $R^3$ is, 1,3-propylene or 1,4-butylene.

T. Bartik, et al. discloses in *Organometallics*, 12 (1993), 164-170, water-soluble phosphines prepared by sulfonating one or more phenyl groups on a tri(aralkyl)phosphine of the formula $P[CH_2)_x(C_6H_5)]_3$, wherein x is 1, 2, 3, or 6.

U.S. Pat. Nos. 4,625,068 and 4,642,388 disclose the use of non-ionic tricycloalkylphosphines, such as tricyclohexylphosphine, in hydroformylation of internal olefins or hindered terminal vinylidenes, respectively.

SUMMARY OF THE INVENTION

In one aspect, this invention provides for a novel class of sulfonated triorganophosphine compounds represented by Formula I:

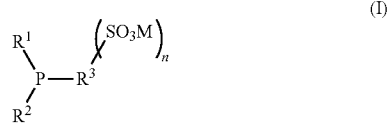

(I)

wherein $R^1$ and $R^2$ each individually represent a monovalent hydrocarbyl or substituted hydrocarbyl radical selected from alkyl, aralkyl, and alicyclic radicals; wherein $R^3$ represents a divalent or polyvalent arylalkylene radical (alternatively, "aralkylene radical"), wherein the alkyl moiety is bonded to the phosphorus atom and the aryl moiety is bonded to the alkyl and is substituted with one or more sulfonate substituents; wherein any aryl group on $R^1$ and $R^2$ and the aryl moiety on $R^3$ are each limited to only one monocyclic aryl ring; and wherein M comprises a monovalent cation, and n is an integer representing a total number of sulfonate substituents, typically, from 1 to 3. As a further requirement, each of $R^1$, $R^2$, and $R^3$ are "bulky" radicals, which means that in each of $R^1$ and $R^2$, the carbon atom attached to the phosphorus atom or a carbon atom directly bonded to the carbon atom attached to the phosphorus atom is additionally bonded to at least 2 other carbon atoms, and in $R^3$ the carbon atom attached to the phosphorus atom is bonded to at least 2 carbon atoms. The aforementioned requirement ensures that $R^1$, $R^2$, and $R^3$ have branching carbon chains that provide for steric bulk.

In a second aspect, this invention provides for a novel complex catalyst or complex catalyst precursor composition comprising a Group 8-10 (formerly Group VIII) transition metal bonded to at least one molecule of ligand comprising Formula I hereinabove, the transition metal optionally being further bonded to carbon monoxide, hydrogen, or both carbon monoxide and hydrogen.

In a third aspect, this invention provides for a novel complex catalyst solution or complex catalyst precursor solution comprising a solvent, a complex catalyst or catalyst precursor composition comprising a Group 8-10 transition metal bonded to at least one molecule of ligand, and optionally further comprising free ligand, wherein the bonded and free ligands are represented by Formula I hereinabove; and wherein optionally the Group 8-10 transition metal may be further bonded to carbon monoxide, hydrogen, or both carbon monoxide and hydrogen.

The following advantages of the invention are mentioned; but should not in any manner place limits on the invention. At the start, the ionically-charged class of compounds claimed herein possesses sufficient water solubility or solubility in appropriate mixtures of water and non-aqueous polar solvents, such that said ionically-charged compound(s) can be easily separated from one or more non-polar reaction products. The separation involves addition of water to the product fluid with subsequent formation of two immiscible liquid phases, one of which is the product phase and the other of which is the catalyst-containing phase. This advantage renders the claimed class of compositions useful for certain hydroformylation processes detailed hereinafter. Accordingly, the novel catalyst composition and novel solution claimed herein comprising the ionically-charged ligand composition of this invention find utility, particularly, in the hydroformylation of long-chain olefinically-unsaturated compounds having from 6 to about 60 carbon atoms, preferably, from about 10 to about 50 carbon atoms, such as, olefinically-unsaturated fatty acids or fatty esters derived from seed oils. Beneficially, the novel hydroformylation catalyst of this invention provides for comparable olefin conversion and product selectivity, as compared with prior art catalysts containing ionically-charged ligands. Moreover, the novel composition provides for improved ligand stability and improved ligand and rhodium recovery and recycling, as compared with prior art ligands containing one or more aryl-phosphorus bonds. Indeed, one of the essential decomposition mechanisms of the prior art ligands involves alkyl-aryl exchange with the aryl radical directly attached to phosphorus. The class of compounds claimed in this invention does not comprise an aryl-phosphorus bond, but rather contains phosphorus bonded only to bulky alkyl groups, thereby essentially eliminating the possibility of alkyl-aryl exchange. Additionally, the bulky alkyl groups $R^1$, $R^2$, and $R^3$ provide for acceptable ligand concentration effect on process reaction rate, which means that a change in ligand concentration does not unacceptably alter the reaction rate.

In a fourth aspect, this invention provides for a novel hydroformylation process comprising contacting one or more olefinically-unsaturated compounds with carbon monoxide and hydrogen in the presence of a Group 8-10 transition metal-ligand complex catalyst, wherein the ligand is represented by the composition of Formula I hereinabove, the contacting being conducted under process conditions sufficient to prepare one or more corresponding aldehyde products. The novel hydroformylation process of this invention finds utility in the production of useful organic intermediates, solvents, and monomers, particularly, mono-, di-, and trialcohols and amines. These monomers can be converted via transesterification into polyester polyols and polyester polyamines that find utility in the manufacture of polyurethane polymers.

In a fifth aspect, this invention comprises a novel class of non-ionic triorganophosphine compounds represented by Formula II:

(II)

wherein $R^1$ and $R^2$ each individually represent a monovalent hydrocarbyl or substituted hydrocarbyl radical selected from alkyl, aralkyl, and alicyclic radicals; wherein $R^3H$ represents a monovalent arylalkyl radical (alternatively, "aralkyl" radical) which is the monovalent analog of the divalent or polyvalent arylalkylene radical $R^3$ of Formula I, while having no sulfonate substituents (such that the one or more sulfonate ions in Formula I are replaced, respectively, with one or more hydrogen atoms in Formula II), and wherein the alkyl moiety is bonded to the phosphorus atom and the aryl moiety is bonded to the alkyl; and wherein any aryl group on $R^1$ and $R^2$ and the aryl moiety on $R^3H$ are each limited to only one monocyclic aryl ring. As a further requirement analogous to the requirement of Formula I, each of $R^1$, $R^2$, and $R^3H$ are "bulky" radicals, which means that in each of $R^1$ and $R^2$, the carbon atom attached to the phosphorus atom or a carbon atom directly bonded to the carbon atom attached to the phosphorus atom is additionally bonded to at least 2 other carbon atoms, and in $R^3H$ the carbon atom attached to the phosphorus atom is bonded to at least 2 carbon atoms.

The class of non-ionic triorganophosphine compounds represented by Formula II can be employed as a precursor to preparing the class of sulfonated triorganophosphine compounds represented by Formula I. Moreover, if desired, the class of triorganophosphine compounds represented by Formula II can be used themselves in hydroformylation processes wherein a non-ionic ligand is desirably employed. Accordingly, in a sixth aspect, this invention provides for a novel hydroformylation process comprising contacting one or more olefinically-unsaturated compounds with carbon monoxide and hydrogen in the presence of a Group 8-10 transition metal-ligand complex catalyst, wherein the ligand is represented by the composition of Formula II hereinabove, the contacting being conducted under process conditions sufficient to prepare one or more corresponding aldehyde products.

DETAILED DESCRIPTION OF THE INVENTION

Figure 1:
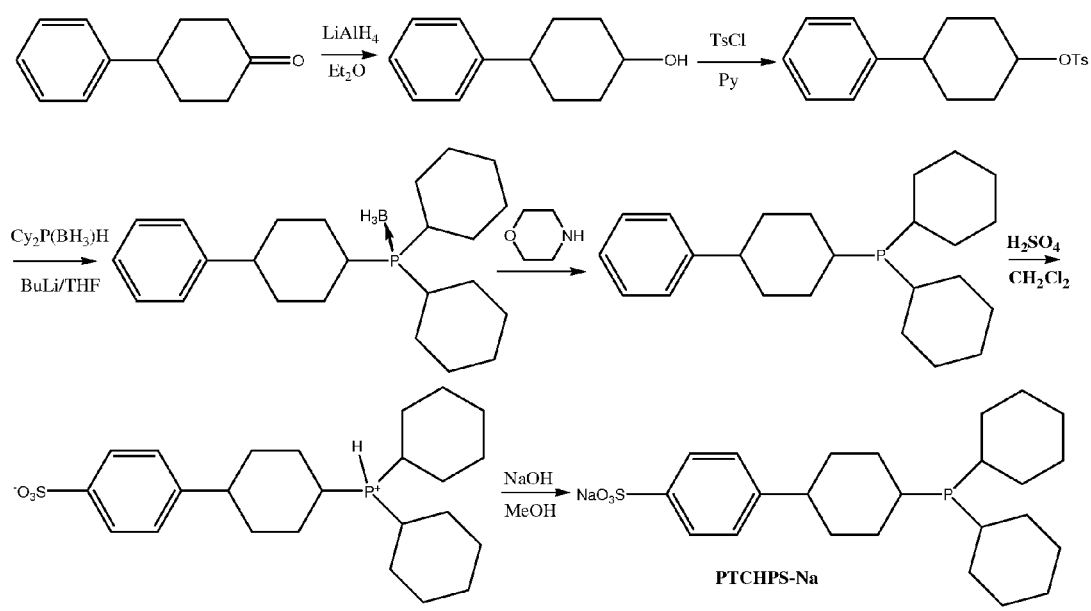
FIG. 1 illustrates a synthetic scheme for preparing sodium 4-[4-(dicyclohexylphosphino)cyclohexyl]benzenesulfonate.

Certain phrases, terms, and words used in this Application are defined hereinafter. When interpreting a meaning of a phrase, term, or word, its definition here governs, unless for a particular use, a different meaning is stated elsewhere in this specification or unless a context of the use of the phrase, term, or word clearly indicates a different meaning is intended from the definitions provided herein.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises "an" olefin can be interpreted to mean that the olefin includes "one or more" olefins.

All percentages, preferred amounts or measurements, ranges and endpoints thereof are inclusive, that is, "a range from 5 to 10" includes 5 and 10. "At least" is equivalent to "greater than or equal to," and "at most" is, thus, equivalent to "less than or equal to." Numbers herein have no more precision than stated. Thus, "115" includes at least from 114.6 to 115.4. All ranges from a parameter described as "at least," "greater than," "greater than or equal to" or similarly, to a parameter described as "at most," "up to," "less than," "less than or equal to," or similarly, are preferred ranges regardless of the relative degree of preference indicated for each parameter. Thus, a range that has an advantageous lower limit combined with a most preferred upper limit is preferred for the practice of this invention. The term "advantageously" is used to denote a degree of preference more than required, but less than is denoted by the term "preferably."

Unless stated otherwise, when an element, material, or step capable of causing undesirable effects is present in amounts or in a form such that it does not cause the effect to an unacceptable degree, that element, material, or step is considered substantially absent for the practice of this invention. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

As used herein, the phrase "having the formula" or "represented by the formula" is not intended to be limiting and is used in the same manner as the term "comprising" is commonly used.

The term "comprising," is synonymous with "including," "containing," or "characterized by," is inclusive or open-ended, and does not exclude additional, unrecited elements, material, or steps. The term "consisting essentially of" indicates that in addition to specified elements, materials, or steps, unrecited elements, materials or steps are optionally present in amounts that do not unacceptably materially affect at least one basic and novel characteristic of the subject matter. The term "consisting of" indicates that only stated elements, materials or steps are present except that unrecited elements, materials or steps are optionally present to an extent that has no appreciable effect, or are substantially absent.

The word "optionally" means "with or without," that is, not mandatory and left to one's choice. As an example, to say "optionally, a non-polar solvent" means with or without a non-polar solvent.

The number of carbon atoms or a range thereof forming a moiety or compound is defined by prefixing the moiety or compound with a formula "$C_m$" or "$C_m$-$C_n$," respectively, wherein m and n are integers. For example, a $C_1$-$C_{10}$ hydrocarbyl means the hydrocarbyl has a number of carbon atoms in a range from one (1) to ten (10) carbon atoms.

Abbreviations and symbols "g," "h," "L," "ml," "mol," "mmol," "NMR," "° C.," "psia (kPa)," and "%" are used, respectively, for "gram," "hour" "liter," "milliliter," "mole," "millimole," "nuclear magnetic resonance," "degree Celsius," "pounds per square inch absolute (kilopascals), and "percent," respectively, and plural forms thereof.

For the purposes of this invention, all citations herein to chemical Group(s) and elements are referenced with respect to *IUPAC Nomenclature of Inorganic Chemistry: IUPAC Recommendations* 2005, Royal Society of Chemistry, 2005, edited by N. G. Connelly and T. Damhus. (For correspondence with the former recommendation, see Periodic Table of the Elements, *CRC Handbook of Chemistry and Physics, 75th* ed., CRC Press, 1994.)

The relevant teachings of each reference cited herein are incorporated to the maximum extent allowed by United States law. In the event of a conflict between a portion of an incorporated reference and this Application, this Application takes precedence.

In the detailed description that follows, several chemical terms are frequently used, which for clarity are defined herein.

The term "hydrocarbyl" refers to a univalent organic radical comprised of carbon and hydrogen atoms and containing from about 1 to about 30 carbon atoms, preferably, from 1 to about 12 carbon atoms, including linear, branched, cyclic, saturated and unsaturated species, such as alkyl, alicyclic, alkenyl, aryl, alkaryl, and aralkyl groups. The term "substituted hydrocarbyl" refers to a hydrocarbyl radical that is substituted with one or more substituents disclosed hereinafter.

The term "hydrocarbylene" refers to a divalent hydrocarbyl radical.

As used herein the term "aromatic" refers to a polyatomic, cyclic, conjugated ring system containing $(4\delta+2)\pi$-electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings. The term "aryl" refers to a monovalent aromatic substituent which may be a single aromatic ring or multiple aromatic rings that are fused together, linked covalently, or linked to a common group such as a methylene or ethylene moiety. Examples of aromatic ring(s) include phenyl, naphthyl, anthracenyl, and biphenyl, among others. Preferred aryl radicals contain one aromatic ring.

The term "arylene" refers to a divalent aryl radical

The term "alkaryl" refers to a monovalent aryl radical with one or more alkyl substituents. The term "alkarylene" refers to a divalent aryl radical with one or more alkyl substituents.

The term "alkyl" refers to a saturated monovalent hydrocarbyl radical, which may be linear, branched, or cyclic (alicyclic). If linear or branched, the radical typically contains from 1 to about 30 carbon atoms, for example, methyl, ethyl, propyl, isopropyl, butyl, iso-butyl, tert-butyl, and the like. If cyclic (alicyclic), the radical typically contains from 4 to about 8 carbon atoms, such as cyclobutyl, cyclopentyl, cyclohexyl, cycloheptyl, and cyclooctyl. Preferably, the linear or branched alkyl radical contains from about 1 to about 12 carbon atoms; and the alicyclic radical contains from about 5 to about 7 carbon atoms, exclusive of carbon-containing substituents.

The term "alkylene" as used herein refers to a linear, branched, or cyclic divalent alkyl radical.

The term "aralkyl" or "arylalkyl" refers to a monovalent alkyl radical substituted with at least one aryl radical. The term "aralkylene" refers to a divalent alkylene radical substituted with at least one aryl radical.

The term "arylalicyclic" refers to an alicyclic radical substituted with at least one aryl group. An example of an arylalicyclic radical is "phenylcyclohexyl" or "phenylcyclopentyl." Typically, the arylalicyclic radical contains greater than about 10 carbon atoms and less than about 20 carbon atoms.

As used herein, any and all of the terms "hydrocarbyl," "hydrocarbylene," "alkyl," "alkylene," "aromatic," "aryl," "arylene," "alkaryl," "alkarylene," "aralkyl," "aralkylene," "alicyclic" and "arylalicyclic" are intended to include substituted variants thereof. The term "substituted" or the words "substituted variants thereof" generally refer to the replacement of at least one hydrogen atom that is bonded to a carbon atom, for example, an alkyl or aryl carbon atom, with a non-hydrogen moiety, for example, a heteroatom or heteroatom-containing substituent, preferably, a halogen (preferably, F), nitrogen, oxygen, or phosphorus. In the detailed description of this invention, it is frequently noted that "arylalicy-clic" radical is substituted with one or more sulfonate ions. The presence of one or more substituents on any particular radical will increase the valency of that radical by one or more. For example, if a monovalent arylalicyclic radical is substituted with one or more sulfonate substituents, the valency of the arylalicyclic radical will increase to divalent or polyvalent, respectively. Other substituents that may be present on any of the radicals include, without limitation, functional groups such as halogen (preferably F), phosphonyl, $C_{1-20}$ alkylamido, imino, hydroxyl, $C_{1-20}$ alkoxy, $C_{5-20}$ aryloxy, $C_{2-20}$ alkoxycarbonyl, $C_{5-20}$ aryloxycarbonyl, formyl, acyl, cyano, cyanato, carbamoyl, epoxy, silyl, siloxy, silanyl, siloxazanyl, and the hydrocarbyl moieties $C_{1-20}$ alkyl, $C_{2-20}$ alkenyl, $C_{2-20}$ alkynyl, $C_{5-20}$ aryl, $C_{5-30}$ aralkyl, and $C_{5-30}$ alkaryl; preferably, cyano, fluoro, trifluoromethyl, trialkylsilyl, alkoxy, carboalkoxy (ester), dialkyl amino, dialkylamido, more preferably, where appropriate in the aforementioned preferred list having $C_{1-15}$ carbon atoms. In addition, the aforementioned functional groups may, if a particular group permits, be further substituted with one or more additional functional groups or with one or more hydrocarbyl moieties, such as those specifically enumerated above.

In one aspect, this invention provides for a novel class of sulfonated triorganophosphine compounds represented by the following Formula I:

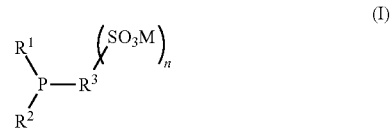

wherein $R^1$ and $R^2$ each individually represent a monovalent hydrocarbyl or substituted hydrocarbyl radical selected from alkyl, aralkyl, and alicyclic radicals; wherein $R^3$ represents a divalent or polyvalent arylalkylene radical (alternatively, "aralkylene radical"), wherein the alkyl moiety is bonded to the phosphorus atom and the aryl moiety is bonded to the alkyl and is substituted with one or more sulfonate substituents; and wherein any aryl group on $R^1$ and $R^2$ and the aryl moiety on $R^3$ are each limited to only one monocyclic aryl ring; and wherein M comprises a monovalent cation, and n is an integer representing a total number of sulfonate substituents, typically, from 1 to 3. As a further requirement, each of $R^1$, $R^2$, and $R^3$ are "bulky" radicals, which means that in each of $R^1$ and $R^2$, the carbon atom attached to the phosphorus atom or a carbon atom directly bonded to the carbon atom attached to the phosphorus atom is additionally bonded to at least 2 other carbon atoms, and in $R^3$ the carbon atom attached to the phosphorus atom is bonded to at least 2 carbon atoms. While not intending to bind the invention to any theory, it is believed that bulky radicals may provide for hydroformylation catalysts comprising only one organophosphine ligand per transition metal atom (as opposed to a plurality of ligands per transition metal atom), which in turn may lead to improved catalyst activity.

In a preferred embodiment, $R^1$ and $R^2$ are each individually a monovalent hydrocarbyl or substituted hydrocarbyl radical containing from 3 to about 30 carbon atoms selected from alkyl, aralkyl, and alicyclic monovalent radicals, with branching at the carbon attached to the phosphorus atom or branching at the carbon adjacent to the carbon attached to the phosphorus atom so as to provide for steric bulk. The alkyl radicals, more preferably, contain from 3 to about 12 carbon atoms, while the arylalkyl radicals, more preferably, contain from 6 to about 12 carbon atoms. The alicyclic radicals may be mono-cyclic, bi-cyclic, or poly-cyclic and preferably, contain from about 3 to about 8 carbon atoms, exclusive of carbon-containing substituents on the ring(s). An illustrative, but non-limiting, list of alkyl radicals represented by the $R^1$ and $R^2$ includes iso-propyl, iso-butyl, sec-butyl, tert-butyl, 2,2-dimethylpropyl, 2-methylbutyl, 1,1-dimethylpropyl, 2-ethylhexyl. Aralkyl radicals include, without limitation, phenylcyclohexyl, 1,2,3,4-tetrahydronaphthyl, phenylcyclopentyl; alicyclic radicals include, without limitation, cyclopentyl, cyclohexyl, cyclooctyl, ethylcyclohexyl, norbornyl, and dicyclopentyl. Moreover, such monovalent hydrocarbon radicals may be substituted with any substituent that does not adversely change the desired result(s) of this invention. Illustrative substituents that may be bound to the monovalent hydrocarbyl radical include those substituents mentioned hereinabove, preferably, cyano, fluoro, trifluoromethyl, trialkylsilyl, alkoxy, carboalkoxy (ester), dialkyl amino, and dialkylamido, more preferably, having 1 to about 15 carbon atoms where appropriate. Even more preferably, $R^1$ and $R^2$ are each individually selected from branched chain alkyl and alicyclic radicals having from 3 to 8 carbon atoms (such as iso-propyl, iso-butyl, neo-pentyl, etc.), cyclohexyl, and norbornyl. Most preferably, $R^1$ and $R^2$ each individually represent a cyclohexyl or norbornyl radical, especially, cyclohexyl.

Preferably, $R^3$ in Formula I is selected from divalent and polyvalent arylalicyclic radicals having greater than 10 carbon atoms and typically less than 20 carbon atoms, which optionally may be substituted with substituents such as those mentioned above, preferably, halide, alkoxy, cyano, and/or alkyl groups. As shown in Formula I, $R^3$ is bonded to at least one sulfonate ($—SO_3^-$) ion attached to the aryl group, which therefore gives rise to the divalency or polyvalency of $R^3$, depending upon whether one or more sulfonate ions, respectively, are present. $R^3H$ in Formula II is identical to $R^3$ in Formula I, with the exception that $R^3H$ is monovalent and contains a hydrogen atom at any carbon that might otherwise be substituted with a sulfonate ion in Formula I. A non-limiting list of $R^3H$ groups suitable in Formula II is set forth hereinafter:

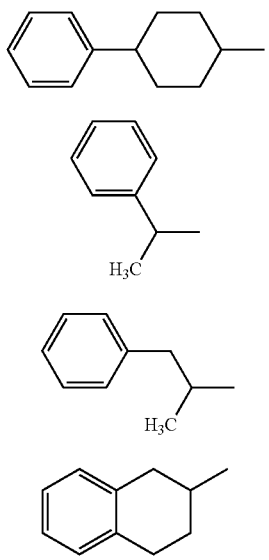

III

IV

V

VI

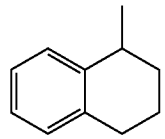

VII

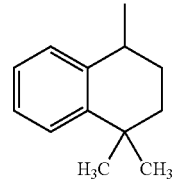

VIII

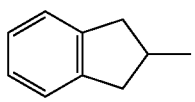

IX

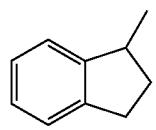

X

In $R^3H$ hereinabove, the alkyl moiety is bonded to the phosphorus atom in the claimed phosphine and the radical contains no sulfonate substituent. In $R^3$ of Formula I, one or more sulfonate species replace one or more hydrogen atoms on an aryl carbon to form the divalent or polyvalent $R^3$ radical and the ionically-charged phosphine shown in Formula I.

More preferably, M in Formula I represents a monovalent metal cation selected from the group consisting of alkali metal ions. Illustrative alkali metal ions include lithium ($Li^+$), sodium ($Na^+$), potassium ($K^+$), rubidium ($Rb^+$), and cesium ($Cs^+$). Preferably, M is sodium or potassium ion. Moreover as noted above, n is preferably 1 or 2.

Preferred sulfonated tertiary phosphine metal salt compounds of Formula I include the following, wherein any monovalent metal ion, preferably another alkali metal ion, can be substituted for the illustrated alkali metal ion:

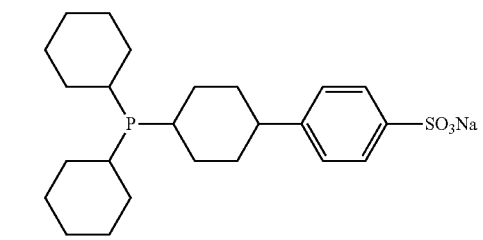

Ligand 1A

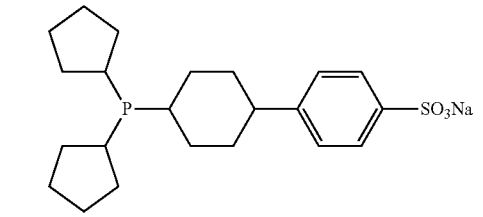

Ligand 2A

Ligand 3A
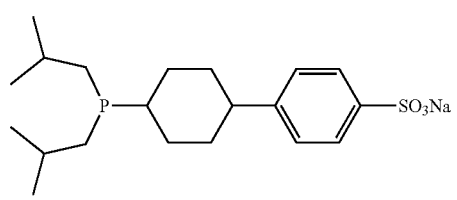
Ligand 4A
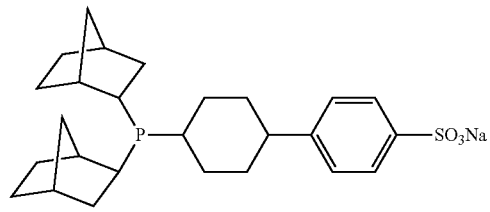
Ligand 5A
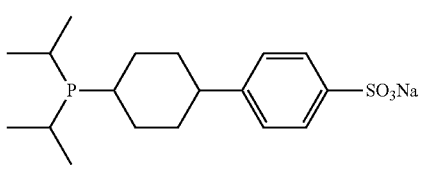
Ligand 6A
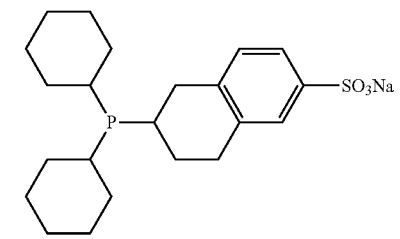
Ligand 7A
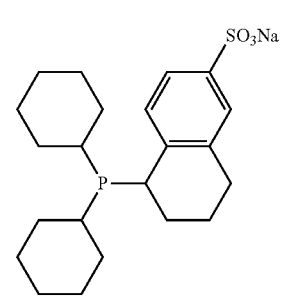
Ligand 7B
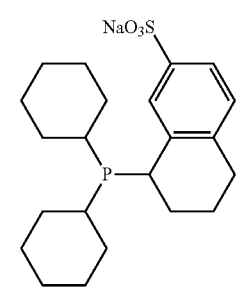
Ligand 8A
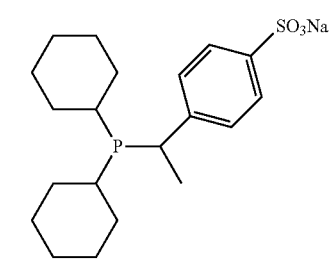
Ligand 9A
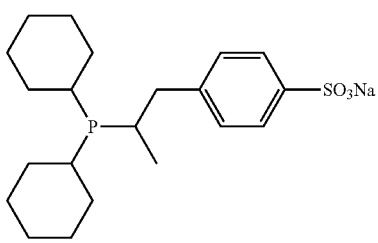
Ligand 10A
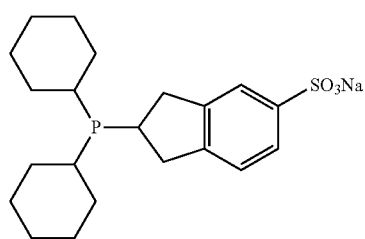
Ligand 11A
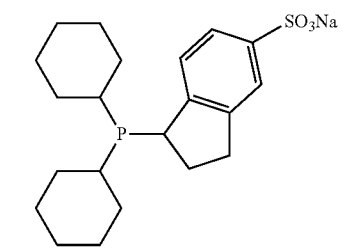
Ligand 12A
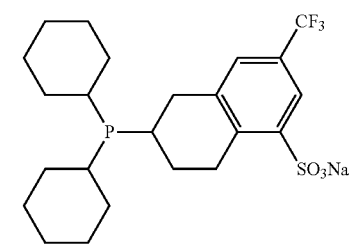
Ligand 13A
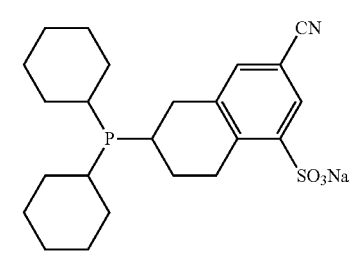

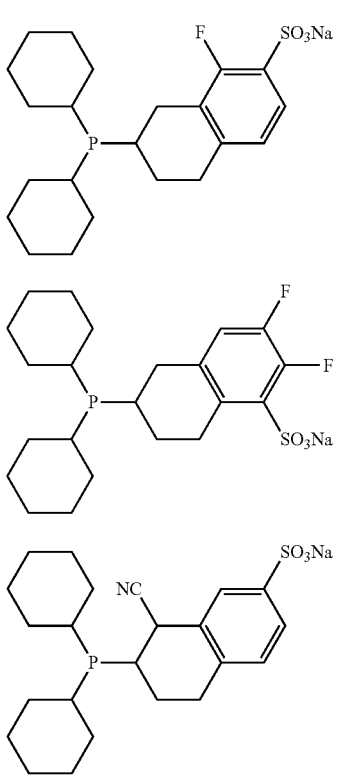

Ligand 14A

Ligand 15A

Ligand 16A

The ionically-charged triorganophosphine (I) of this invention can be prepared from a borane-protected phosphorus compound, more specifically, a boron-protected dihydrocarbylphosphine, described, for example, by J. McNulty and Y. Zhou in *Tetrahedron Letters*, 2004, 45, 407-409, incorporated herein by reference. In contrast to unprotected phosphines, these borane-protected phosphines are resistant to oxidation. Metalation of the borane-protected dihydrocarbylphosphine with a lithium reagent results in a borane-protected dihydrocarbylphosphide. A coupling reaction of the borane-protected dihydrocarbylphosphide with an electrophilic aralkyl compound leads to the desired (dihydrocarbyl)(aralkyl)phosphine. The general methodology finds basis in the art as disclosed by B. Mohr, D. M. Lynn, and R. H. Grubbs, in *Organometallics* 1996, 15, 4317-4325; although the disclosed methodology has not, to our knowledge, been applied to the materials incorporated into this invention. A key step in the synthesis involves formation of a new phosphorus-carbon bond (P—C) by coupling the borane-protected dihydrocarbylphosphide with an aralkyl tosylate. After deprotection, the resulting neutral phosphine comprising a (dihydrocarbyl)(aralkyl)phosphine having the alkyl group bonded to the phosphorus atom of the phosphine and having one or more aryl groups pendant to the alkyl group is readily sulfonated, after which extraction and optional neutralization yield the claimed product of Formula I. Without neutralization, the (dihydrocarbyl)(aralkyl)phosphine sulfonate exists in an acidic form typically as a zwitterion; whereas after neutralization, the phosphine sulfonate is converted to a salt form. The general procedure will be described with particular reference to the synthesis of the particular species depicted in FIG. 1, namely, the synthesis of the sodium 4-[4-(dicyclohexylphosphino)cyclohexyl]benzenesulfonate, $Cy_2PC_6H_{10}C_6H_4SO_3Na$ (Ligand 1A).

1. Preparation of Aralkyl Tosylate ($R^3H$-Ts) from Tosyl Halide and Arylalkanol ($R^3H$—OH)

At the start, an aralkanol ($R^3HOH$), such as 4-phenylcyclohexanol, where $R^3H$ is the monovalent alkyl analog of $R^3$ in Formula I, is obtained commercially or prepared by reducing the corresponding aralkanone, for example 4-phenylcyclohexanone, using lithium aluminum hydride ($LiAlH_4$) in a suitable solvent, such as tetrahydrofuran or diethyl ether, under conventional reaction conditions. A general protocol for this type of reaction is given in B. S. Furniss, A. J. Hannaford, P. W. G. Smith, and A. R. Tatchell, *Vogel's Textbook of Practical Organic Chemistry*, 5th edition, 1989, Wiley & Sons, New York, pp. 525-526. Thereafter, reaction of the aralkanol, for example 4-phenylcyclohexanol, with a tosylating agent, such as tosyl chloride (TsCl), is effected in accordance with conventional procedures for alcohol tosylation, as described, for example, by G. W. Kabalka, M. Varma, R. E. Varma, *J. Org. Chem.* 1986, 51, 2386-2388, incorporated herein by reference. The resulting aralkyl tosylate ($R^3H$-Ts), for example, 4-phenylcyclohexyl p-toluenesulfonate, provides a suitable leaving group (Ts) for the reaction with a borane-protected dihydrocarbyl phosphine $R^1R^2P(BH_3)H$, wherein $R^1$ and $R^2$ are defined as in Formula I.

2. Preparation of a Metallated Borane Protected Dihydrocarbylphosphide $\{R^1R^2P(BH_3)Li\}$ from Dialkylphosphine $R^1R^2PH$ A borane-adduct is prepared separately from the reaction of a commercial precursor (dihydrocarbyl)phosphine ($R^1R^2PH$) and boron hydride in tetrahydrofuran ($BH_3.THF$) and purified by crystallization from a suitable solvent, such as pentane. See, for example, B. Mohr, D. M. Lynn, R. H. Grubbs, in *Organometallics* 1996, 15, 4317-4325, incorporated herein by reference, for suitable reaction conditions. The metalation of the resulting borane-protected phosphine $\{R^1R^2P(BH_3)H\}$ is then conducted with an alkylmetal compound, preferably, alkyl lithium, more preferably, n-butyl lithium, in a suitable solvent, such as tetrahydrofuran, at a temperature ranging from about −85° C. to about +10° C., preferably at about −78° C., to yield a metallated borane-protected phosphide $\{R^1R^2P(BH_3)Li\}$.

3. Coupling of the Metallated Borane-Phosphide $\{R^1R^2P(BH_3)Li\}$ with Aralkyl Tosylate ($R^3H$-Ts) to Yield Borane-Protected Precursor Phosphine $\{R^1R^2P(BH_3)$—$R^3H\}$ The metallated borane-protected (dihydrocarbyl)phosphide $\{(R^1R^2P(BH_3)Li\}$ is reacted at a temperature ranging from −80° C. to about +95° C., preferably at about −70° C., for a time from about 30 minutes to about 5 hours, preferably, about 1.5 hours, and then at about +67° C.±5° C. with the aralkyl tosylating agent ($R^3H$-Ts), the reaction being monitored by phosphorus nuclear magnetic resonance spectroscopy ($^{31}P$ NMR) until all of the phosphide is consumed. The reaction may be refluxed for a time ranging from about 6 hours to about 3 days to effect complete conversion of the phosphide. The product obtained is a (dihydrocarbyl)(aralkyl)phosphide borohydride adduct $\{R^1R^2R^3HP(BH_3)\}$.

4. Removal of Borane Protection to Obtain Non-Sulfonated Precursor Compound $R^1R^2PR^3H$ Subsequently, the borane group is cleaved from the (dihydrocarbyl)-(aralkyl)phosphide borohydride adduct $\{R^1R^2R^3HP(BH_3)\}$ by treatment with morpholine at a temperature ranging from about 50° C. to about 110° C., and the resulting crude unprotected phosphine is crystallized, for example, from any suitable solvent, such as a mixture of ethanol and acetonitrile, to yield a neutral or non-ionic (dihydrocarbyl)(aralkyl)phosphine, for example, dicyclohexyl(4-phenylcyclohexyl)phosphine (Ligand 1).

The generic non-ionic (dihydrocarbyl)(aralkyl)phosphine is represented by Formula II:

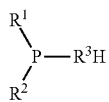
(II)

wherein $R^1$, $R^2$, and $R^3H$ are as defined hereinbefore. Preferred species of non-ionic (dihydrocarbyl)(aralkyl)phosphines include the following compositions represented by Precursor Ligands 1 to 16 as follows:

Ligand 1

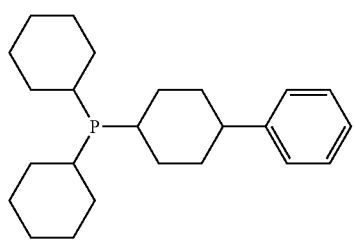

Ligand 2

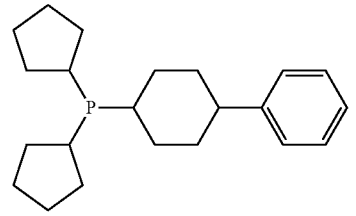

Ligand 3

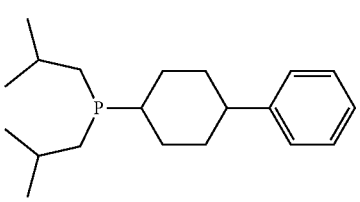

Ligand 4

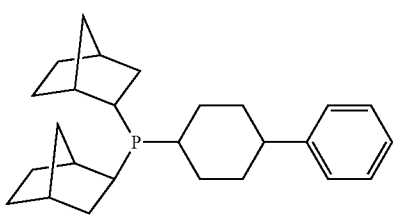

Ligand 5

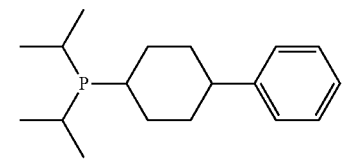

-continued

Ligand 6

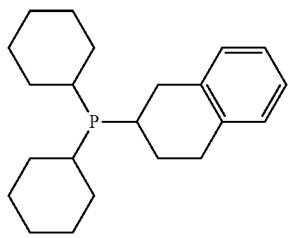

Ligand 7

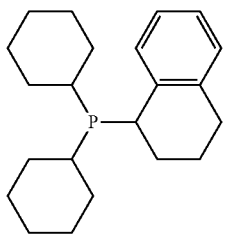

Ligand 8

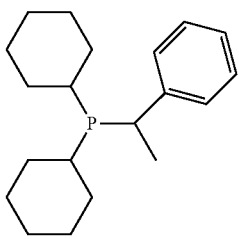

Ligand 9

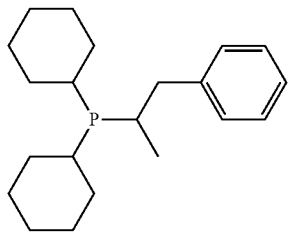

Ligand 10

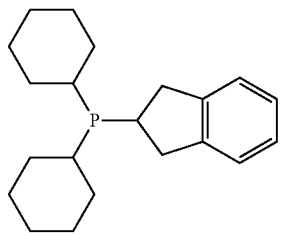

Ligand 11

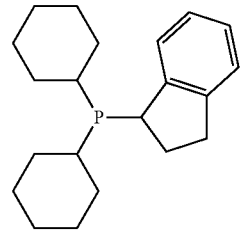

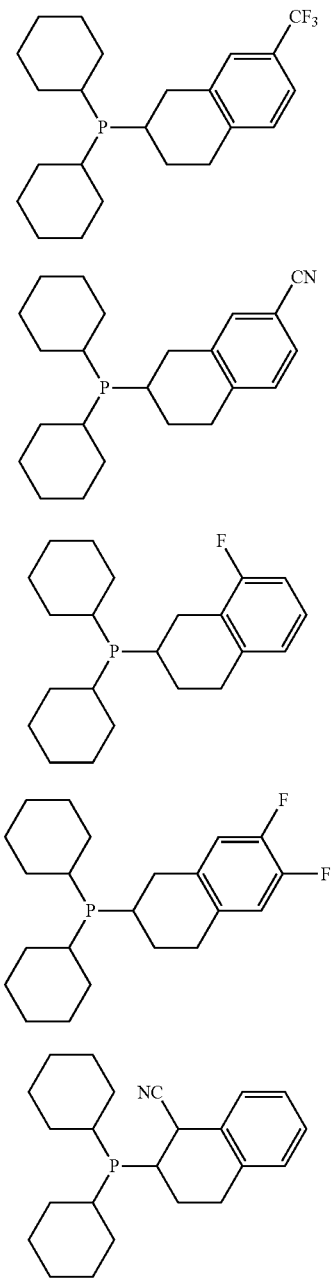

Ligand 12
Ligand 13
Ligand 14
Ligand 15
Ligand 16

5. Sulfonation of the Non-Sulfonated Phosphine Precursor $R^1R^2PR^3H$ to Sulfonated Phosphine $R^1R^2P$—$R^3$—$SO_3M$ The sulfonation of deprotected non-ionic phosphine precursor compounds, $R^1R^2PR^3H$ employs sulfonation procedures known in the art as described, for example, in S. Ahrland, J. Chatt, N. R. Davies, A. A. Williams, *J. Chem. Soc.* 1958, 276-282; and P. J. Roman, Jr., D. P. Paterniti, R. F. See, M. R. Churchill, J. D. Atwood, *Organometallics* 1997, 16, 1484-1490; and R. Gartner, B. Cornils, H. Springer, P. Lappe, U.S. Pat. No. 4,483,802; all references incorporated herein by reference. In contrast to the sulfonation of arylphosphines, which requires fuming sulfuric acid ($SO_3$—$H_2SO_4$ mixture), sulfonation of a remote aryl group (i.e., aryl with no phosphorus-aryl bond) can be achieved with concentrated sulfuric acid, typically, 96 percent sulfuric acid, as described by T. Bartik, B. Bartik, B. E. Hanson, I. Guo, I. Toth, *Organometallics* 1993, 12, 164-170, incorporated herein by reference. Typically, (dihydrocarbyl)(aralkyl)phosphine mono-sulfonate in the acidic form is soluble in chlorinated hydrocarbons and sufficiently insoluble in water to allow for a simple isolation procedure. For example, dilution of the sulfonation reaction mixture with water and extraction with methylene chloride or chloroform affords the product (signal at ca. 10-20 ppm in $^{31}P$ NMR), which is the zwitterionic form of the (dihydrocarbyl)(aralkyl)phosphine monosulfonate acid. (The term "zwitterion" (from the German "Zwitter"—"hybrid," "hermaphrodite") is a chemical compound that is electrically neutral but carries formal positive and negative charges on different atoms. In this instance, the phosphorus atom is protonated and carries a +1 charge, while the sulfonate group is deprotonated and carries a −1 charge.). The zwitterionic form can be neutralized using a stoichiometric amount of base, such as a Group 1 alkali metal hydroxide, dissolved in a suitable solvent, such as a lower alkanol or water; and the neutralized product can be filtered, freed of solvent, and dried in vacuum to yield the solid sulfonated phosphine salt of Formula I.

The isolation and purification (when necessary) of all the intermediates and products in FIG. 1 can be achieved by any suitable method, including crystallization, vacuum distillation, and column chromatography; but advantageously crystallization is sufficiently effective and preferred over chromatography and distillation. The structures of the intermediates and product(s) can be determined via conventional analytical tools known to the skilled person, including particularly $^{31}P$ and $^1H$ nuclear magnetic resonance spectroscopy (NMR). The purity of intermediates can be verified by thin layer chromatography (TLC), high performance liquid chromatography (HPLC), and gas phase chromatography (GC) and ionic chromatography (IC) analyses, as known to the skilled person.

The composition of this invention of Formula I finds application as a ligand in transition metal complex catalysts and catalyst precursors that are used in carbonylation processes, preferably, hydroformylation processes. Accordingly, in a second aspect this invention provides for an entirely new class of complex catalysts and complex catalyst precursor compositions that comprise a Group 8, 9, or 10 transition metal bonded to one ligand represented by Formula I. Optionally, the Group 8-10 transition metal may also be bonded to carbon monoxide, hydrogen, or both carbon monoxide and hydrogen. The Group 8-10 transition metal that makes up the complex catalyst or catalyst precursor composition of this invention includes transition metals selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, with the preferred metals being ruthenium, rhodium, cobalt, and iridium, more preferably, rhodium and cobalt, and most preferably, rhodium. The term "complex" as used herein is taken to mean a coordination compound formed by the union of one or more ligands, herein one or more ligands of Formula I, with the Group 8-10 metal. Inherently, the ligand(s) is/are electronically rich, since each ligand possesses one phosphorus donor atom having one available or unshared pair of electrons that is capable of forming a coordinate covalent bond with the Group 8-10 transition metal. The oxidation state of the Group 8-10 metal may be any available oxidation state, either electronically neutral (zero) or electronically deficient (positive valence), that allows for bonding to the ligand. Moreover, the oxidation state of the Group 8-10 transition metal as well as the overall oxidation state of the coordination complex or complex precursor may vary during use in the hydroformylation process. The number of available coordination sites on the Group 8-10 transition metal is well known in the art and may range typically from about 4 to about 6. Optionally, the Group 8-10 transition metal may be additionally bonded to carbon monoxide, hydrogen, or both carbon monoxide and hydrogen.

In a third aspect, this invention can be described as a novel transition metal complex catalyst or catalyst precursor solution comprising an organic solvent, a solubilized Group 8-10 transition metal-ligand complex, and optionally, free ligand, wherein the free and bound ligands are represented by Formula I hereinabove. Such novel solutions may be prepared by forming a solution comprising an organic solvent, free ligand, and a Group 8-10 transition metal source material, such as the corresponding transition metal oxide, hydride, carbonyl, salt, or organotransition metal complex described hereinafter; and thereafter subjecting such solution to reaction conditions sufficient to bind at least a portion of the ligand to the Group 8-10 transition metal. Optionally, carbon monoxide and hydrogen may be dissolved in the solution and bonded to the Group 8-10 transition metal.

The Group 8-10 transition metal-ligand complex catalyst of this invention can be synthesized by methods known in the art. For instance, a Group 8-10 transition metal hydrido-carbonyl(ligand) catalyst can be preformed and introduced into the reaction medium of a hydroformylation process. Standard identification methods may be used to identify the complex catalyst or catalyst precursor composition, including for example, elemental analysis, mass spectroscopy, infrared spectroscopy, and $^1H$, $^{31}P$, and/or $^{13}C$ NMR spectroscopy.

Preferably, the Group 8-10 transition metal-ligand complex catalyst of this invention is derived from a Group 8-10 transition metal source material that is introduced into the carbonylation reaction medium for in situ formation of the active catalyst. For example, rhodium source materials, such as, rhodium acetylacetonate, rhodium dicarbonyl acetylacetonate, $Rh_2O_3$, $Rh_4(CO)_{12}$, $[RhCl(CO)_2]_2$, $Rh_6(CO)_{16}$, $Rh(NO_3)_3$, and the like may be introduced into the carbonylation reaction medium along with the ligand for the in situ formation of the active catalyst. In a preferred embodiment, rhodium dicarbonyl acetylacetonate is employed as a rhodium source material and reacted with the ligand in the presence of a solvent to form a rhodium-ligand complex catalyst precursor composition, which is introduced into the reactor along with excess free ligand for the in situ formation of the active catalyst. In any event, it is sufficient for the purpose of this invention to understand that carbon monoxide, hydrogen, and ligand are all ligands that are capable of being complexed with the Group 8-10 transition metal, for example, rhodium, and that an active Group 8-10 transition metal-ligand complex catalyst is present in the reaction medium under the conditions of the hydroformylation process. The reaction conditions sufficient for formation of the complex catalyst or catalyst precursor in most cases will be similar to the hydroformylation reaction conditions described hereinbelow.

In a fourth aspect, this invention provides for a carbonylation process, which comprises contacting an organic compound capable of being carbonylated with carbon monoxide under reaction conditions in the presence of the aforementioned Group 8-10 transition metal-ligand complex catalyst wherein the ligand is represented by Formula I. Such processes may include the carbonylation of organic compounds, such as olefins, acetylenes, alcohols, and activated chlorides, with carbon monoxide, and optionally, either hydrogen, alcohol, amine, or water, as well as ring closure reactions of functionally unsaturated compounds, for example, unsaturated amides, with carbon monoxide. Exemplary carbonylation processes include, for example, simple carbonylation (insertion of carbonyl in absence of other reactants), hydroformylation, hydroacylation (intermolecular and intramolecular), hydrocyanation, hydroamidation, hydroesterification, and hydrocarboxylation processes. In a preferred embodiment, the carbonylation process also contains free ligand in addition to the ligand bonded to the Group 8-10 transition metal. Preferably, the carbonylation process involves a hydroformylation process, more preferably, the hydroformylation of an olefinically-unsaturated compound with carbon monoxide in the presence of hydrogen and the transition metal-ligand complex catalyst under reaction conditions to prepare one or more corresponding aldehydes (or formyl-substituted product(s)). Hydroformylation is also known under various other names including the "oxo" process, the "oxo" reaction, "oxonation," the "Roelen reaction." The processing techniques employed in the hydroformylation process of this invention correspond to any of the known processing techniques employed in conventional hydroformylation processes, as described hereinafter.

The successful practice of the hydroformylation process of this invention does not depend and is not predicated upon the precise formula of the catalytically active metal complex species, which may be present in a mononuclear, dinuclear, or higher nuclearity form. Indeed, the precise formula of the catalytically active metal ligand complex may be difficult to determine analytically. Although not intended to be bound to any theory or mechanistic discourse, it appears that the active catalytic species in its general form comprises the Group 8-10 transition metal in complex combination with one ligand of Formula I, optionally further in combination with carbon monoxide. The ultimate composition of the active complex may also contain one or more additional ligands, such as hydrogen, or an anion satisfying the coordination sites or nuclear charge of the transition metal obtained typically from the starting transition metal material. Illustrative additional ligands include alkyl, aryl, substituted aryl, $CF_3^-$, $C_2F_5^-$, $CN^-$, $R'_2PO^-$, $R'P(O)(OH)O^-$ (wherein each R' is alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2=CHCH_2^-$, $C_6H_5CN$, $CH_3CH=$, $NO$, $NH_3$, pyridine, $(C_2H_5)_3N$, mono-olefins, diolefins, tri-olefins, tetrahydrofuran, and the like. Of course, the active complex species is preferably free of any additional organic ligand or anion that might poison the catalyst and have an unacceptable adverse effect on the catalyst performance, such as possibly halogen atoms and sulfur atoms with a low degree of oxidation, such as mercaptans.

Any amount of complex catalyst can be employed in the hydroformylation process, provided that the amount is sufficient to catalyze the desired hydroformylation reaction. Advantageously, the concentration of complex catalyst provides for a concentration of Group 8-10 transition metal of greater than about 10 parts per million (ppm), preferably, greater than about 25 ppm, by weight calculated as free metal. Advantageously, the concentration of complex catalyst provides for a concentration of Group 8-10 transition metal of less than about 1,000 ppm, preferably, less than about 800 ppm, and more preferably, less than about 600 ppm, by weight calculated as free metal.

The olefinic reactants to be used in the hydroformylation process of this invention can be any terminally or internally olefinically-unsaturated aliphatic hydrocarbon, including straight chain, branched chain, and cyclic formulas. Such olefins contain advantageously from 2 to about 60 carbon atoms and one or more unsaturated carbon-carbon (C=C) double bonds. Long-chain olefinically-unsaturated aliphatic hydrocarbons having from 6 to about 60 carbon atoms, are preferred, and from about 10 to about 50 carbon atoms are more preferred. Moreover, such olefins may contain substituents that essentially do not adversely interfere with the hydroformylation process, including, for example, carbonyl, carbonyloxy, hydroxy, oxycarbonyl, halo, alkyoxy, aryl, haloalkyl, cyano, and the like. Non-limiting examples of suitable olefinic unsaturated reactants include, for example, alpha olefins, internal olefins, alkyl alkenoates, alkenyl alkanoates, alkenyl alkyl ethers, alkenols, olefinically-unsaturated fatty acids, and olefinically-unsaturated fatty acid esters; the latter unsaturated fatty acid and fatty acid ester species including naturally-occurring and genetically modified seed oils. A non-limiting list of suitable olefinically-unsaturated compounds includes ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethylhexene, styrene, 3-phenyl-1-propene, butadiene, 1,3-cyclohexadiene, 1,4-cyclohexadiene, 1,7-octadiene, 3-cyclohexyl-1-butene, allyl alcohol, hex-1-en-4-ol, oct-1-ene-4-ol, vinyl acetate, allyl acetate, 3-butenyl acetate, vinyl propionate, 1-vinyl-3-cyclohexene, allyl propionate, allyl butyrate, methyl methacrylate, 3-butenyl acetate, vinyl ether, vinyl methyl ether, allyl ethyl ether, n-propyl-7-octenoate, methyl 1-decenoate, 3-butenenitrile, 5-hexenamide, methyl oleate, castor oil, soybean oil, canola oil, and sunflower oil, including high oleic variations of the aforementioned oils. Mixtures of any of the aforementioned olefinic starting materials can be employed, if desired. Preferably, the hydroformylation is useful for the production of aldehydes by the hydroformylation of alpha olefins containing from 2 to about 60 carbon atoms ($C_2$-$C_{60}$), or internal olefins containing from 4 to about 50 carbon atoms ($C_4$-$C_{50}$), and more preferably, from about 10 to about 50 carbon atoms ($C_{10}$-$C_{50}$) as found in unsaturated fatty acids and esters derived from seed oils.

The hydroformylation process of this invention is preferably conducted in the presence of an organic solvent for the Group 8-10 transition metal complex catalyst. Any suitable solvent that does not unduly interfere with the hydroformylation process can be used including those types of solvents commonly used in prior art carbonylation processes. By way of illustration, suitable solvents for rhodium-catalyzed hydroformylation processes include those disclosed, for example, in U.S. Pat. Nos. 3,527,809; 4,148,830; 5,180,854, and 5,929,289, the aforementioned citations being incorporated herein by reference. Non-limiting examples of suitable solvents include saturated hydrocarbons (e.g., pentane, octane, decane), aromatic hydrocarbons (e.g., benzene, toluene, xylene), ethers (e.g., tetrahydrofuran), nitriles (e.g., benzonitrile, acetonitrile, propionitrile), aldehydes (including higher boiling hydroformylation products and aldehyde liquid condensation products), ketones broadly including piperidones, pyrrolidones and pyrrolidinones (e.g., N-methylpyrrolidinone, N-methyl piperidone, 1,5-dimethyl-2-pyrrolidone, 2-hydroxyethyl pyrrolidone, N-cyclohexyl pyrrolidone), amides (e.g., dimethylformamide, dimethylacetamide, N-dimethylpropionamide), sulfoxides (e.g., dimethyl sulfoxide), sulfones (e.g., dimethyl sulfone, sulfolane), as well as ionic liquids and supercritical carbon dioxide. Mixtures of two or more solvents may also be employed. When the ligand employed is an ionic ligand, it is preferred to use a non-aqueous, aprotic, polar solvent selected from any in the list hereinabove, more preferably, N-methylpyrrolidinone (NMP). When the ligand employed is a non-ionic ligand, it is preferred to use a nonpolar solvent selected from any in the list hereinabove. The amount of solvent is not especially critical and need only be sufficient to provide the reaction medium with the desired amount of Group 8-10 transition metal concentration. Advantageously, the amount of solvent ranges from about 5 percent to about 95 percent by weight, based on the total weight of the reaction medium.

The hydroformylation process of this invention may optionally be conducted in the presence of free ligand of Formula I, that is, ligand that is not complexed with the Group 8-10 transition metal. While the use of free ligand may not be required, it is preferred. The free and complexed ligands can be identical species; or if desired, the free and complexed ligands can be different species falling within the scope of Formula I (if an ionic ligand is desired) or Formula II (if a non-ionic ligand is desired). While the carbonylation process of this invention may be carried out in any excess amount of free ligand, advantageously at least one mole of free ligand per mole of Group 8-10 transition metal is present in the reaction medium. For most purposes, preferably, the amount of ligand per mole of Group 8-10 transition metal is greater than about 1.1/1, more preferably, greater than about 1.3/1 is employed. Preferably, the amount of ligand per mole of Group 8-10 transition metal is less than about 100/1, more preferably, less than about 50/1. The aforementioned ratios correspond to the sum of both the free and complexed ligand. Make-up ligand can be added during the hydroformylation process at any time and in any suitable manner, so as to maintain a predetermined concentration of free ligand in the reaction medium.

The reaction conditions for effecting hydroformylation can be chosen from any of those conditions conventionally used and known for such processes. The total gas pressure of hydrogen, carbon monoxide, and olefinic unsaturated reactant in the hydroformylation process advantageously may range from greater than about 1 psia (7 kPa) to less than about 10,000 psia (68,948 kPa). Preferably, the total pressure of hydrogen, carbon monoxide, and olefinic unsaturated reactant is less than about 2000 psia (13,790 kPa), and more preferably, less than about 1500 psia (10,342 kPa). More specifically, the carbon monoxide partial pressure of the hydroformylation process of this invention is advantageously greater than about 1 psia (7 kPa), preferably, greater than about 3 psia (21 kPa). The carbon monoxide partial pressure of the hydroformylation process of this invention is advantageously less than about 1000 psia (6,8948 kPa), preferably, less than about 750 psia (5171 kPa). The hydrogen partial pressure is advantageously greater than about 5 psia (35 psia), preferably, greater than about 10 psia (69 kPa). The hydrogen partial pressure is advantageously less than about 1000 psia (6,8948 kPa), preferably, less than about 750 psia (5171 kPa). Advantageously, the $H_2$/CO molar ratio of gaseous hydrogen to carbon monoxide may be greater than about 1/10, and preferably, equal to or greater than about 1/1. Advantageously, the $H_2$/CO molar ratio may be less than about 100/1, and preferably, equal to or less than about 10/1.

Further to the hydroformylation process of this invention, the reaction temperature will depend upon the particular olefinic reagent and metal catalyst employed, as well as the efficiency desired. Advantageously, hydroformylations at reaction temperatures of greater than about 30° C., and preferably, greater than about 40° C., are suitable. Advantageously, hydroformylations at reaction temperatures of less than about 150° C., and preferably, less than about 130° C. are suitable.

The hydroformylation process of this invention can be carried out in the liquid or gas phase, preferably, in one liquid phase, which can more preferably involve a continuous liquid phase recycle stream comprising the transition metal-ligand complex catalyst and any free ligand back to the hydroformylation reactor.

In the preferred hydroformylation process of this invention, the olefin conversion is advantageously greater than about 65 mole percent. For the purposes of this invention, "olefin conversion" is defined as the mole percentage of olefin feed converted to all products. Olefin conversion will vary depending upon the specific olefin reactant, the specific form of the catalyst, and the specific process conditions employed. Preferably, the olefin conversion is greater than about 75 mole percent, more preferably, greater than about 80 mole percent.

Likewise, in the preferred hydroformylation process of this invention, the yield of aldehyde product is advantageously greater than about 60 mole percent. For the purposes of this invention, "yield" is defined as the mole percentage of aldehyde product produced, based on the total moles of olefin fed to the process. Again, the yield of aldehyde produced will vary based on the specific olefin reactant, the specific form of the catalyst, and the specific process conditions employed. Preferably, the yield of aldehyde is greater than about 75 mole percent, more preferably, greater than about 80 mole percent, even more preferably, greater than about 85 mole percent, and most preferably, greater than about 90 mole percent.

In the preferred process wherein the reactant olefin comprises one or more long-chain olefinically-unsaturated compounds, preferably, a mixture of unsaturated fatty acids or unsaturated fatty acid esters, the effluent stream from the hydroformylation reactor can be mixed with water so as to induce phase separation to produce a polar phase comprising water, non-aqueous organic solvent, e.g., N-methylpyrrolidinone, the transition metal-ligand complex catalyst, and optional free ligand, wherein the complexed and free ligands are ionically-charged ligands of Formula I, and a non-polar phase comprising one or more formyl-substituted products, preferably one or more formyl-substituted fatty acids or fatty acid esters, and any non-polar solvent(s) that may be present. The polar phase is typically recycled back to the reactor after evaporation of water, while the non-polar phase is worked up to recover purified aldehyde product(s) for downstream use.

The following examples are illustrative of the present invention and are not to be regarded as limiting thereof. Variations in operational parameters, such as reactants, process conditions, forms of the transition metal-ligand complex catalyst, and ligand species, all falling within the scope of the claims, will be apparent to those skilled in the art based on the description and examples contained herein. All of the parts, percentages, and proportions are given by mole percent, unless otherwise indicated.

EXAMPLE 1

Preparation of Neutral Ligand 1 and Ionic Ligand 1A (With Reference to FIG. 1)

(a) Preparation of 4-phenylcyclohexanol

4-Phenylhexanone (1.74 g; 10 mmoL) is mixed with 1M lithium aluminum hydride ($LiAlH_4$) solution in tetrahydrofuran (THF) (10 mL; 10 mmoL). The reaction mixture is stirred and refluxed for 6 hrs. After the starting ketone is consumed as determined by thin-layer chromatography (TLC) and gas phase chromatography (GC), the reaction mixture is carefully quenched with water (40 mL) whereupon a precipitate forms. Then, hydrochloric acid (10 mL) is added to dissolve the precipitate, and the solution is twice extracted with diethyl ether (20 mL twice). The combined ether portions are dried with $Na_2SO_4$, and the solvent is evaporated to yield 4-phenylcyclohexanol (1.71 g; 74%). The purity and identity of the compound are established by TLC and GC using an authentic sample of the material obtained from Lancaster Company.

(b) Preparation of 4-phenylcyclohexyl 4-methylbenzenesulfonate (4-phenylcyclohexanol tosylate)

Commercial chloroform (Aldrich) is freed from stabilizing ethanol by passing the chloroform through a column of alumina. 4-Phenylcyclohexanol (28.3 g; 160 mmol.) is dissolved in the chloroform (150 mL) and the resulting solution is cooled in an ice bath (0° C.). Pyridine (25.3 g; 25.9 mL; 320 mmol.) is added to the solution, followed by the addition of p-toluenesulfonyl chloride (45.8 g; 240 mmol.) in small portions with constant stiffing. The reaction mixture is left overnight. TLC (hexane-ethyl acetate 15:1) shows that the starting 4-phenylcyclohexanol is consumed completely. Ether (500 mL) and water (150 mL) are added, and the organic layer is washed successively with 300 mL of 2N HCl, 5% $NaHCO_3$, and water and then dried with $Na_2SO_4$. TLC exhibits three spots, the major one having the lowest $R_f$. The solvent is removed in a rotary evaporator, and the crude tosylate (70.4 g) is dissolved in 125 mL of hexane-ethylacetate (4:1) mixture upon heating and then left to crystallize in the freezer at −20° C. White product is collected and dried in vacuum, yield 40.6 g (76%), identified as 4-phenylcyclohexyl 4-methylbenzenesulfonate. TLC (hexane-ethyl acetate 15:1)—one spot, $R_f$=0.16. $^1$H NMR ($\delta$ $CDCl_3$, ppm): 1.2-2.2 (m, 8H, cyclohexyl), 2.46 (s, 3H, $CH_3$), 2.48 (m, 1H, PhCH), 4.50 (m, 1H, TsOCH), 7.1-7.3 (m, 5H, Ph), 7.35 and 7.83 (two d, J=8.1 Hz, 4H, $C_6H_4$).

(c) Preparation of dicyclohexyl(4-phenylcyclohexyl)phosphine-borane, $Cy_2P(BH_3)C_6H_{10}Ph$ Dicyclohexylphosphine-borane, $Cy_2PH(BH_3)$, prepared according to the procedure disclosed in B. Mohr, D. M. Lynn, R. H. Grubbs, *Organometallics* 1996, 15, 4317-4325 (69.9 g; 0.309 mol.), is placed in a 2 L three-neck flask containing a reflux condenser, purged with nitrogen and dissolved in fresh anhydrous THF (1 L). The resulting solution is cooled to about −70° C., and n-butyllithium (213 mL of a 1.6 M solution in hexane; 0.34 moL, 1.1 equivalent) is added slowly via syringe over a period of 1.5 h. The bath is removed, and the reaction mixture is stirred for 2.5 h at room temperature. Complete conversion of the starting material to the corresponding lithium phosphide $Cy_2P(BH_3)Li$ is verified by $^{31}$P NMR.

Then the solution is cooled to −70° C. again, and 4-phenylcyclohexyl 4-methylbenzenesulfonate, $PhC_6H_{10}OTs$ (122.5 g; 0.37 mol), prepared above, in THF (350 mL) is added using a syringe for 1.5 h in the flow of nitrogen. The reaction mixture is warmed to room temperature and refluxed for 18 h. TLC shows formation of a new spot with $R_f$=0.50 along with the remaining starting tosylate and a baseline compound (hexane-ethyl acetate 15:1). $^{31}$P NMR analysis exhibits a new major signal. Longer reaction time did not increase the proportion of the new NMR signal in the mixture. The solution is filtered; THF is removed in a rotary evaporator and the residue is dried for 1 h in vacuum. The resulting solid (172 g) is extracted 3 times with 500 mL of a hexane-ethyl acetate (50:1) mixture, filtered, and the solvents are evaporated. The residue is crystallized from 2 L of hexane to give a white solid material, which is washed with 150 mL of hexane. Yield of dicyclohexyl(4-phenylcyclohexyl)phosphine-borane, $Cy_2P(BH_3)C_6H_{10}Ph$, is 68.6 g (60%). $^{31}P\{^1H\}$ NMR ($\delta$ $C_6D_6$, ppm): 29.03 and 29.60 (broad); $^1$H NMR ($\delta$ $C_6D_6$, ppm): 1.003 (broad m, 3H, $BH_3$), 1.2-2.2 (m, 31H, cyclohexyl), 2.78 (t, J=3.5 Hz, 1H, PhCH), 7.0-7.3 (m, 5H, Ph).

(d) Preparation of dicyclohexyl(4-phenylcyclohexyl)phosphine, $Cy_2PC_6H_{10}Ph$ (Ligand 1)

$Cy_2P(BH_3)C_6H_{10}Ph$ (29.0 g; 78.3 mol), prepared in step (c) is dissolved in morpholine (grade "redistilled", 700 mL) and heated at 110° C. for 2 h in the flow of nitrogen. TLC (hexane-ethyl acetate 10:1) shows complete consumption of the starting material. Morpholine is evaporated at 40 mm Hg and 75° C.; the distillation is continued until a solid appears in the flask. The residue is crystallized from a methanol (500 mL) and benzene (30 mL) mixture. After the mixture is kept in the freezer for 2 days, the precipitate is filtered off, dried in vacuum for 2 h. Yield of dicyclohexyl(4-phenylcyclohexyl)phosphine, $Cy_2PC_6H_{10}Ph$, is 25.4 g (91%). $^{31}P\{^1H\}$ NMR ($\delta$ $C_6D_6$, ppm): −2.96; $^1H$ NMR ($\delta$ $C_6D_6$, ppm): 1.1-2.2 (m, 31H, cyclohexyl), 2.80 (m, 1H, PhCH), 7.0-7.3 (m, 5H, Ph).

(e) Preparation of 4-[4-(dicyclohexylphosphino)cyclohexyl]benzenesulfonic acid, $Cy_2PC_6H_{10}C_6H_4SO_3H$ Sulfuric acid (96 percent, 200 mL) is added slowly under nitrogen to dicyclohexyl(4-phenylcyclohexyl)phosphine (25 g; 70.2 mol), prepared above, at −70° C. The mixture is warmed to room temperature and stirred for 3 hrs. The reaction mixture is added carefully to 2 L of water purged with nitrogen and cooled to about +5° C. The water solution is extracted 4 times with methylene chloride (250 mL each, four times). The solid present initially in the water solution disappears during the course of extraction. Methylene chloride is evaporated, a white residue is dried in vacuum for 1 h to give 25.1 g (82%) of the product 4-[4-(dicyclohexylphosphino)cyclohexyl]benzenesulfonate in the acid form, $Cy_2PC_6H_{10}C_6H_4SO_3H$. $^{31}P\{^1H\}$ NMR ($\delta$ $CD_2Cl_2$, ppm): 13.07; $^1H$ NMR ($\delta$ $CD_2Cl_2$, ppm): 1.2-2.2 (m, 31H, cyclohexyl), 2.60 (m, 1H, PhCH), 7.24 and 7.59 (dd, J=8.2 Hz, 4H, aromatic).

(f) Preparation of sodium 4-[4-(dicyclohexylphosphino)cyclohexyl]benzenesulfonate, $Cy_2PC_6H_{10}C_6H_4SO_3Na$ (Ligand 1A)

Sodium hydroxide (1.82 g; 45.5 mol.) is dissolved in 50 mL of methanol and added dropwise under nitrogen to 4-[4-(dicyclohexylphosphino)-cyclohexyl]benzenesulfonic acid (19.86 g; 45.5 mmol.) in 200 mL of methanol. The pH of the resulting system upon mixing with water is about 9.4. The mixture in methanol is filtered, the solvent is evaporated and the residue is dried in vacuum to constant weight. Yield of sodium 4-[4-(dicyclohexyl-phosphino)cyclohexyl]benzenesulfonate, $Cy_2PC_6H_{10}C_6H_4SO_3Na$, is 20.4 g (98%). $^{31}P\{^1H\}$ NMR ($\delta$ $CD_3OD$, ppm): −1.28. $^1H$ NMR ($\delta$ $CD_3OD$, ppm): 1.2-2.2 (m, 31H, cyclohexyl), 2.74 (m, 1H, PhCH), 7.34 and 7.74 (dd, J=8.2 Hz, 4H, aromatic).

EXAMPLE 2

Preparation of Neutral Ligand 2

(a) Preparation of dicyclopentyl(4-phenylcyclohexyl)phosphine-borane, $Cpy_2P(BH_3)C_6H_{10}Ph$ The product is made similarly to its analog in Example 1 from dicyclopentyl-phosphine-borane (10.6 g; 57.5 mmol.), n-butyl lithium (39.5 mL of 1.6 M solution; 63.3 mmol.) and 4-phenylcyclohexyl 4-methylbenzenesulfonate (22.8 g; 68.9 mmol.). Yield 14.5 g (74%). $^{31}P\{^1H\}$ NMR ($\delta$, $C_6D_6$, ppm): 33.22 and 33.83 (broad); $^1H$ NMR ($\delta$, $C_6D_6$, ppm): 0.944 (m, 3H, $BH_3$), 1.2-2.2 (m, 27H, cyclopentyl+cyclohexyl), 2.82 (m, 1H, PhCH), 7.0-7.25 (m, 5H, Ph).

(b) Preparation of dicyclopentyl(4-phenylcyclohexyl)phosphine, $Cpy_2PC_6H_{10}Ph$ (Ligand 2)

The phosphine is made similarly to its analog in Example 1 from the borane precursor dicyclopentyl(4-phenylcyclohexyl)phosphine-borane (0.60 g; 1.75 mmol.), and morpholine (4.5 mL). Yield 0.55 g (95%). $^{31}P\{^1H\}$ NMR ($\delta$, $C_6D_6$, ppm): −0.95. $^1H$ NMR ($\delta$, $C_6D_6$, ppm): 1.1-2.5 (m, 27H, cyclopentyl+cyclohexyl), 2.74 (m, 1H, PhCH), 7.0-7.33 (m, 5H, Ph).

EXAMPLE 3

Preparation of Neutral Ligand 3

(a) Preparation of di-isobutyl(4-phenylcyclohexyl)phosphine-borane, i-$Bu_2P(BH_3)C_6H_{10}Ph$ The product is made similarly to its analog in Example 1 from di-isobutylphosphine-borane (10.1 g; 62.9 mmol.), n-butyl lithium (43.2 mL of 1.6 M solution; 69.2 mmol.) and 4-phenylcyclohexyl 4-methylbenzenesulfonate (25.0 g; 75.5 mmol.). Yield 5.3 g (29%). $^{31}P\{^1H\}$ NMR ($\delta$, $C_6D_6$, ppm): 18.63 and 19.18 (broad).

(b) Preparation of di-isobutyl(4-phenylcyclohexyl)phosphine, i-$Bu_2PC_6H_{10}Ph$ (Ligand 3)

The product is made similarly to its analog in Example 1, from its borane precursor di-isobutyl(4-phenylcyclohexyl)phosphine-borane (5.3 g; 16.6 mmol.) and morpholine (100 mL). Yield 3.8 g (73%). $^{31}P\{^1H\}$ NMR ($\delta$, $C_6D_6$, ppm): −40.09; $^1H$ NMR ($\delta$, $C_6D_6$, ppm): 1.0-2.25 (m, 27H, isobutyl+cyclohexyl), 2.56 (m, 1H, PhCH), 7.05-7.27 (m, 5H, Ph).

EXAMPLE 4

Preparation of Neutral Ligand 4 and Ionic Ligand 4A (a) Preparation of di(bicyclo[2.2.1]heptan-2-yl)(4-phenylcyclohexyl)phosphine-borane, $Nor_2P(BH_3)C_6H_{10}Ph$ The product is made similarly to its analog in Example 1 from dinorbornylphosphine-borane (5.28 g; 20 mmol.), butyl lithium (15 mL of 1.6 M solution; 24 mmoL) and 4-phenylcyclohexyl 4-methylbenzenesulfonate (8.60 g; 26 mmoL). Yield 4.35 g (53%). $^{31}P\{^1H\}$ NMR ($\delta$, $C_6D_6$, ppm): 30.65 and 31.16 (broad); $^1H$ NMR ($\delta$, $C_6D_6$, ppm): 0.966 (m, 3H, $BH_3$), 1.1-2.2 (m, 36H, norbornyl+cyclohexyl), 2.80 (m, 1H, PhCH), 7.0-7.3 (m, 5H, Ph).

(b) Preparation of di(bicyclo[2.2.1]heptan-2-yl)(4-phenylcyclohexyl)phosphine, $Nor_2PC_6H_{10}Ph$ (Ligand 4)

The product is made similarly to its analog in Example 1 from its borane precursor di(bicyclo[2.2.1]heptan-2-yl)(4-phenylcyclohexyl)phosphine-borane (1.04 g; 2.5 mmol.) and morpholine (8.0 mL). Yield 0.92 g (90%). The product is a mixture of three isomers: endo-endo, endo-exo and exo-exo. $^{31}P\{^1H\}$ NMR ($\delta$, $C_6D_6$, ppm): 2.95, 4.75, and 4.92.

(c) Preparation of sodium 4-{4-[di(bicyclo[2.2.1]heptan-2-yl)phosphino]cyclohexyl}benzenesulfonate $Nor_2P(BH_3)C_6H_{10}C_6H_4SO_3Na$ (Ligand 4A)

$Nor_2P(BH_3)C_6H_{10}Ph$ (0.5 g; 1.2 mmol.) is mixed with 96%-sulfuric acid (1 mL) and stirred at room temperature for 2 h. The mixture is poured into 25 mL of water and extracted with methylene chloride (5 mL×4). The solvent is evaporated, the residue is dried in vacuum for 1 h to give 0.5 g of the product. This intermediate (0.5 g; 1.0 mmol.) is mixed with sodium hydroxide (0.04 g; 1.0 mmol.) in 5 mL of methanol, stirred and filtered. The pH of the resulting solution diluted with water is about 9. Methanol is evaporated, the residue is dried in vacuum to give 0.49 g (96%) of the product as a mixture of three isomers (endo-endo, endo-exo and exo-exo). $^{31}P\{^1H\}$ NMR ($\delta$, $CD_3OD$, ppm): 4.09, 5.87 and 5.94; $^1H$ NMR (δ, CD$_3$OD, ppm):1.1-2.3 (m, 36H, norbornyl+cyclohexyl), 3.02 (m, 1H, PhCH), 7.410 and 7.765 (dd, J=8.4 Hz, 4H, aromatic).

EXAMPLES 5-9

Evaluation of Sulfonated Ligand 1A and Neutral Ligands 1-4 in Propylene Hydroformylation A series of examples is designed to evaluate Ligand 1A and Neutral Ligands 1-4, prepared hereinabove, in the hydroformylation of propylene. Each evaluation is conducted according to the following procedure. Rhodium(I) dicarbonyl acetylacetonate (12.6 mg 0.048 mmol) and the corresponding Ligand (L/Rh=5/1) are placed in a nitrogen box in a 50 ml glass bottle capped with a septum. The bottle is purged with nitrogen, and N-methylpyrrolidinone (NMP) (20 g) is added. The mixture is stirred until a homogenous yellow solution forms. The solution is charged to a Parr reactor (80 ml), purged with nitrogen, pressurized with syngas (CO+H$_2$=1:1), and activated for 45 min at 90° C. and 100 psi. Then, the autoclave is pressurized to 120 psi with CO/H$_2$/C$_3$H$_6$ (1:1:1), the pressure valves are closed, and then the time elapsed for a drop in pressure of 5 psi is noted. Then, the pressure is adjusted back to 120 psi, and another time period is noted for a drop in pressure of 5 psi. This procedure is iterated over 10 times, and the data are used to calculate the hydroformylation reaction rate similar to the protocol in U.S. Pat. No. 4,283,562. Then, the reaction mixture is analyzed by GC and $^{31}$P NMR. The results are presented in Table 1.

TABLE 1

| Example | Ligand[1] | Time for 5 psi pressure drop (s) | Normal/Iso Ratio[2] |
|---|---|---|---|
| 5 | Ligand 1 | 21 | 1.27 |
| 6 | Ligand 2 | 23 | 1.14 |
| 7 | Ligand 3 | 35 | 1.48 |
| 8 | Ligand 4 | 23 | 1.15 |
| 9 | Ligand 1A | 22 | 1.25 |
| CE-1 | DCHPP | 23 | 1.22 |
| CE-2 | DCHPPMS | 26 | 1.26 |

[1]DCHPP = dicyclohexylphenylphosphine; DCHPPMS = dicyclohexylphenylphosphine monosulfonate sodium salt.
[2]"Normal/Iso" Ratio is the molar ratio of linear (normal) to branched (iso) aldehyde products formed. Normal product is n-butyraldehyde; iso product is iso-butyraldehyde.

COMPARATIVE EXPERIMENTS 1 and 2

For comparative purposes with Examples 5-9, the procedure of those examples is repeated using a neutral ligand of the prior art, dicyclohexylphenylphosphine (DCHPP, comparative experiment 1) and an ionic ligand of the prior art, dicyclohexylphenylphosphine monosulfonate sodium salt (DCHPPMS, comparative experiment 2). Results are shown in Table 1. When comparative experiments CE-1 and CE-2 are compared with Examples 5-9, it is seen that the ligands of the present invention provide comparable activity and comparable ratios of normal/iso isomeric products as the ligands of the prior art.

EXAMPLE 10

Sulfonated Ligand 1A Evaluation with Soy Methyl Ester at L/Rh=10/1

In this example Ligand 1A, a sodium salt of phenyltricyclohexylphosphine monosulfonate prepared as in Example 1 hereinabove, is tested in the hydroformylation of a mixture of methyl esters of mono-, di-, and tri-unsaturated fatty acid esters derived from soy oil (P&G Chemicals, Cincinnati, Ohio). The ester feedstock is passed through a column of alumina prior to use to remove any peroxides. The ligand is provided as a 0.05 M solution in N-methylpyrrolidinone (NMP). Rhodium (I) dicarbonyl acetylacetonate is provided to the reaction as a 0.05 M solution in NMP. The ligand solution (2.268 ml) is mixed with rhodium (I) dicarbonyl acetylacetonate (0.228 ml) and the soy methyl esters (1.50 ml) in a pressure reactor under a nitrogen atmosphere. The ligand (L)/Rh molar ratio is 10/1; the Rh concentration is 300 parts per million (ppm). The reactor is sealed, pressurized, and heated to 75° C. Hydroformylation is conducted at 400 psi (CO/H$_2$=1:1) and stopped after 3 h. The mixture is analyzed by GC with the results shown in Table 2.

TABLE 2

[1] Hydroformylation of Soy Methyl Esters

| | Example | | |
|---|---|---|---|
| | CE-3 | Ex. 10 | Ex. 11 |
| Ligand (L) | DCHPPMS[2] | Ligand 1A[2] | Ligand 1A[2] |
| (L/Rh mole ratio) | (10/1) | (10/1) | (5/1) |
| Olefin Conversion (mole %) | 91 | 70 | 83 |
| Aldehyde selectivity (mole %) | 87 | 65 | 78 |

[1] [Rh] = 300 parts per million (ppm); 75° C.; 400 psi (CO/H$_2$ 1:1); 3 hrs.
[2]DCHPPMS = dicyclohexylphenylphosphine monosulfonate sodium salt; Ligand 1A = sodium 4-[4-(dicyclohexylphosphino)cyclohexyl]benzenesulfonate, Cy$_2$PC$_6$H$_{10}$C$_6$H$_4$SO$_3$Na

EXAMPLE 11

Evaluating Sulfonated Ligand 1A with Soy Methyl Esters at L/Rh=5/1

Ligand 1A is evaluated in the hydroformylation of soy methyl esters in the manner described in Example 10, with the exception that the quantity of rhodium is decreased by 50 percent and the L/Rh molar ratio is only 5/1. Results are shown in Table 2.

COMPARATIVE EXPERIMENT 3

Example 10 is repeated with the exception that a ligand of the prior art, namely, dicyclohexylphenylphosphine monosulfonate sodium salt, DCHPPMS, is used in place of Ligand 1A. Results are shown in Table 2. When comparative experiment CE-3 is compared with Examples 10 and 11, it is seen that the ionic ligand of the present invention is somewhat less active toward soy oil hydroformylation as compared with the prior art ligand, but nevertheless comparable in aldehyde selectivity (Example 11). The lower olefin conversion is acceptable in light of the increased stability of the claimed ligand against alkyl-aryl exchange, as shown below.

EXAMPLE 12

Ligand Stability Using Continuous Flow Hydroformylation

Figure 2:
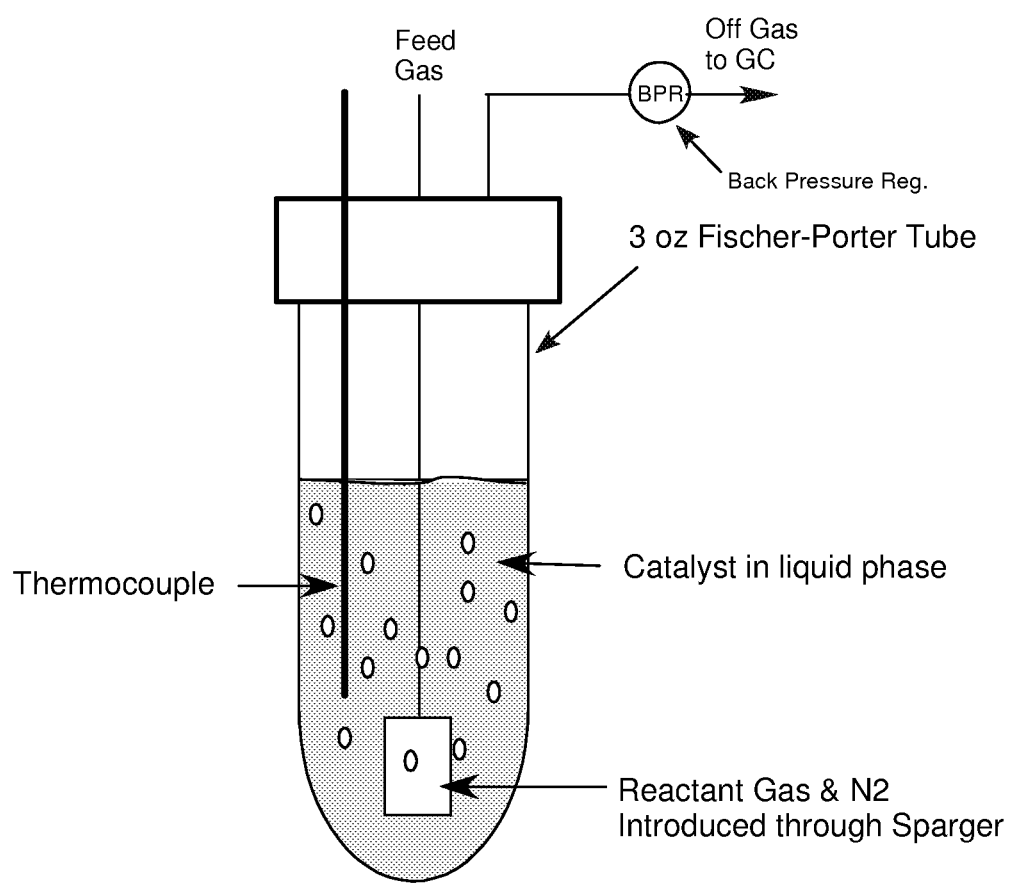
FIG. 2 illustrates a continuous-flow reactor used in testing the non-ionic triorganophosphine composition in a hydroformylation process.

A continuous flow reactor is used for screening long-term catalyst activity and stability. With reference to FIG. 2, a glass reactor (100 mL), fitted with a feed gas input line, a thermocouple for measuring temperature, a vent line, and a rubber septum, is charged with approximately 20 mL of a catalyst solution. The reactor temperature is controlled by a silicone oil bath, and the reactor pressure is controlled with a back-pressure regulator located in the vent line. Feed gases (olefin, hydrogen, carbon monoxide) and nitrogen are fed to the reactor via the feed tube, which ends in a sparger. Feed gases are supplied to the reactor at rates that exceed the consumption rates, such that a vent flow of unreacted gases, which along with nitrogen, helps to strip the product out of the reactors.

The outgoing gases carry the stripped products through the back-pressure regulators into a gas chromatograph for qualitative and quantitative analysis. Hydroformylation is performed by constantly delivering a propylene/syngas mixture ($C_3H_6$:CO:$H_2$) to produce a mixture of n-butyraldehyde and i-butyraldehyde. Further description of the continuous flow reactor is incorporated by reference from Z. Lysenko, B. R. Maughon, M. Mokhtarzadeh, M. L. Tulchinsky, *J. Organometal. Chem.* 2006, 691, 5197-5203.

The catalyst solution is prepared in a nitrogen box using a 25 mL glass bottle with a rubber septum. Rh(CO)$_2$acac (12.6 mg; 0.049 mmol) and a neutral ligand of this invention, specifically, dicyclohexyl(4-phenylcyclohexyl)phosphine (Ligand 1) (174.5 mg; 0.49 mmol), are dissolved in N-methyl-2-pyrrolidinone (20 g). Anhydrous N-methyl-2-pyrrolidinone is sparged with nitrogen prior to mixing with the catalyst. The catalyst solution is quickly charged into a wide needle syringe and discharged into the reactor under a nitrogen purge. The catalyst is sparged with nitrogen for 15 min at room temperature and then tested at 100° C. and 20 psi of propylene and 80 psi of syngas mixture (1:1) for 20 days. The catalyst activity remains steady and no dicyclohexylpropylphosphine, the expected "alkyl-alkyl" exchange product, is observed during the course of the run, as measured within the limits of the GC detector.

COMPARATIVE EXPERIMENT 4 (a-f)

A design set of 6 experiments are conducted to test the stability of a neutral ligand of the prior art, namely, a dicycloalkylarylphosphine, more specifically, dicyclohexyl-phenylphosphine (DCHPP). Six solutions containing a rhodium catalyst prepared with DCHPP are evaluated for hydroformylation of propylene in a continuous flow reactor. Each catalyst solution is prepared in a nitrogen box using a 25 mL glass bottle with a rubber septum. In comparative experiment CE-4a, Rh(CO)$_2$acac (15.1 mg; 0.059 mmol) and DCHPP (80.2 mg; 0.293 mmol) are dissolved in tetraglyme (20 g). Tetraglyme is sparged with nitrogen prior to mixing with the catalyst. Other solutions are prepared similarly with varying quantities of the same ingredients as shown in Table 3 (b-f). The catalyst solution is quickly charged into a wide needle syringe and discharged in the nitrogen purged reactor. The catalyst is sparged with nitrogen for 15 min at room temperature and then tested at 100° C. under a propylene/syngas mixture for 9 days. The reactor solution is sampled after 2, 3, 6, and 9 days to determine ligand degradation products, specifically, dicyclohexylpropylphosphine. Results are shown in Table 3.

TABLE 3

Continuous flow reactor study of the DCHPP phenyl-propyl exchange[1,2]

| Test No. | Rh(CO)$_2$acac | DCHPP | P(H$_2$) | P(CO) | P(C$_3$H$_6$) | Pr-Ph exchange, % Days | | | |
|---|---|---|---|---|---|---|---|---|---|
| CE-4 | (mg) | (mg) | kPa | kPa | kPa | 2 | 3 | 6 | 9 |
| a | 15.1 | 80.2 | 276 | 276 | 69 | — | 0.8 | 3.4 | 9.2 |
| b | 15.1 | 160.3 | 276 | 276 | 69 | — | — | — | 1.8 |
| c | 30.2 | 160.3 | 276 | 276 | 69 | 1.1 | 2.8 | 5.4 | 10.7 |
| d | 30.2 | 320.6 | 276 | 276 | 69 | — | — | 0.5 | 1.2 |
| e | 22.7 | 181.9 | 138 | 276 | 69 | — | — | — | 1.8 |
| f | 22.7 | 181.9 | 552 | 276 | 69 | — | 1.0 | 4.4 | 6.3 |

[1]DCHPP = dicyclohexylphenylphosphine
[2]Pr-Ph exchange = propyl-phenyl exchange In all tests the alkyl-aryl exchange produced dicyclohexylpropylphosphine via the following alkyl-aryl exchange reaction:

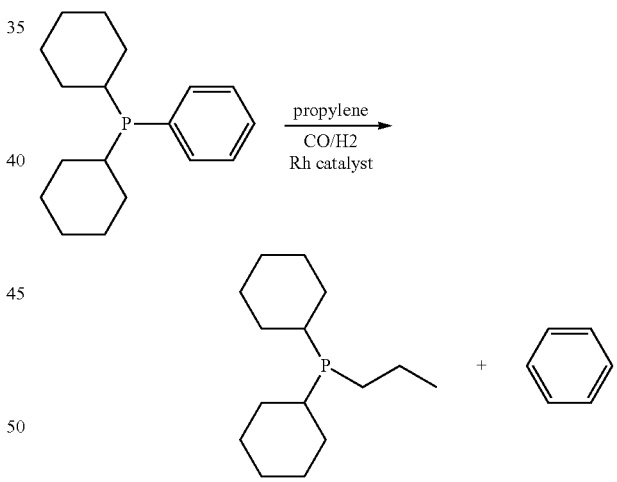

The extent of this ligand degradation pathway depends upon process conditions, but is observed for all comparative experiments CE-4 (a-f). The degradation product accumulates with time. By comparison, Example 12 shows that the claimed non-ionic ligand precursor phosphine composition of this invention exhibits no corresponding "alkyl-alkyl" exchange over a continuous test lasting 20 days. It is noted that the alkyl-aryl exchange depends upon an aryl-phosphorus bond and not upon the sulfonate group. Consequently, the respective "alkyl-alkyl" exchange of the corresponding ionically-sulfonated composition of Formula 1A is not expected to be any different from that shown by its non-ionic phosphine precursor of Formula 1.

EXAMPLE 13

1-Decene Hydroformylation in a Continuous Pilot Plant

Figure 3:
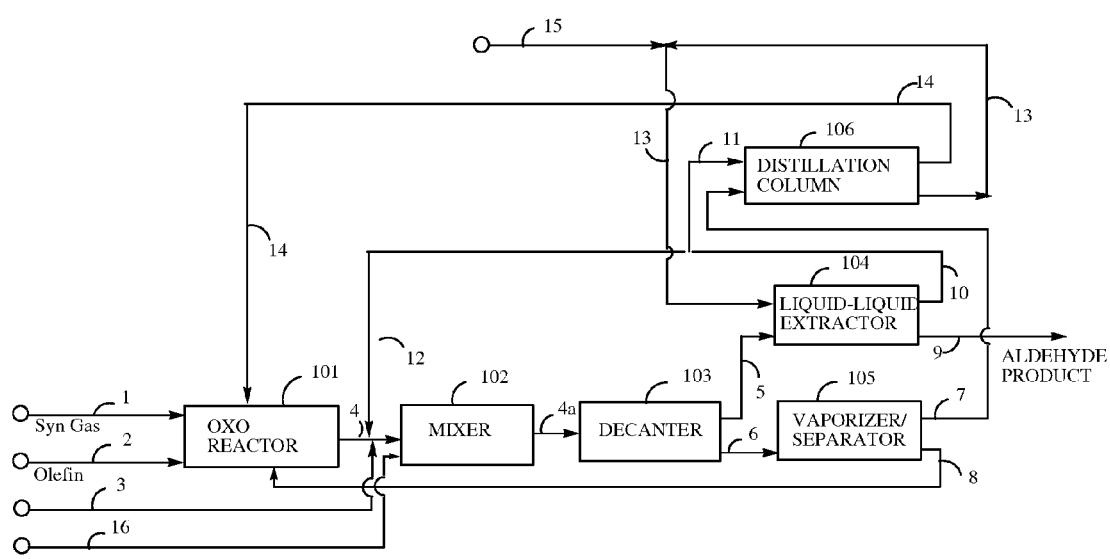
FIG. 3 illustrates a flow diagram for the hydroformylation of an olefin in the presence of a catalyst with separation of an aldehyde product by phase separation and recycle of a catalyst stream back to the hydroformylation reactor.

The hydroformylation process is conducted in a continuous liquid recycle manner for 5 days using an apparatus similar to the apparatus disclosed in Example 6 of U.S. Pat. No. 5,180,854. With reference to FIG. 3, synthesis gas (CO and $H_2$) and 1-decene are fed through lines 1 and 2, respectively, into a hydroformylation zone 101 comprising a series of three sequentially-interconnected continuous stirred tank reactors (Reactors 1, 2, and 3, not shown in Figure), which each contain a rhodium-ligand complex catalyst of this invention, free ligand of this invention, and a polar organic solubilizing agent (NMP), wherein a product mixture is formed comprising, in addition to the aforementioned components, one or more aldehyde products. All or a portion of the corresponding liquid aldehyde containing non-aqueous hydroformylation reaction product is continuously withdrawn from the last reactor in series (Reactor 3) of the hydroformylation zone 101 and fed via line 4 into a phase separation system comprising a mixer (102), decanter (103), liquid-liquid extractor (104), and vaporization columns (105, 106). Water and optionally a non-polar hydrocarbon are added to said withdrawn reaction product via lines 3 and 12, and thoroughly mixed therewith in mixer 102. Gas composition and pressure in the mixer are regulated via gas line 16. The resultant aqueous composition is conveyed from the mixer 102 via line 4a into a liquid decanter vessel 103, wherein said treated composition settles into two distinct liquid phases, namely, a non-polar phase comprising the aldehyde product(s), unconverted 1-decene if any, and the non-polar hydrocarbon additive of line 3, and a polar phase comprising the rhodium-ligand complex, free ligand, the polar organic solubilizing agent, and the added water. The aldehyde containing non-polar phase is removed from the decanter vessel 103 via line 5 and conveyed to a liquid-liquid extractor 104. Polar compounds that are present in the aldehyde-containing nonpolar phase are removed with the aid of water (and a rhodium scavenger if desired, such as, the ligand used in the hydroformylation step via line 15 and then into line 13) added to said liquid-liquid extractor 104 via line 13; and the desired purified liquid aldehyde product is obtained and recovered from the extractor via line 9. The aqueous liquid polar phase in decanter 103 containing the rhodium-ligand complex and free ligand are removed via line 6 and conveyed to a vaporizer/separator 105 for removal of the water; and the non-aqueous composition obtained therefrom containing rhodium-ligand complex and free ligand is recycled to the hydroformylation reactor via line 8. The water recovered from said vaporizer/separator 105 is recycled to the distillation column 106 via line 7. A portion of the aqueous composition obtained from said liquid-liquid extractor 104 via line 10 is conveyed via line 12 into line 4 containing the non-aqueous hydroformylation reaction product composition for input to the mixer. Likewise, a portion of said aqueous composition from line 10 is conveyed via line 11 to a distillation column 106, wherein the water is separated from the polar organic solubilizing agent. The purified water from said distillation column 106 is returned to said liquid-liquid extractor 104 via line 13, while the polar organic solubilizing agent obtained from distillation column 106 is recycled to the hydroformylation reactor 101 via line 14.

The catalyst is prepared by placing rhodium dicarbonyl acetylacetonate (2.55 g) and sodium 4-[4-(dicyclohexyl-phosphino)cyclohexyl]-benzenesulfonate (Ligand 1A herein, 22.55 g) into a 2 liter bottle, evacuating, and purging with nitrogen. The application of vacuum, followed by charging of nitrogen is repeated three times. Then anhydrous N-methyl-pyrrolidinone (600 g) is transferred into the bottle. The mixture is stirred under nitrogen for 2 hours until a homogeneous solution is formed. This solution, containing 5 mole equivalents of Ligand 1A per mole of Rh, is fed into the hydroformylation reaction zone into Reactors 1, 2, and 3, and mixed with 1-decene under the syngas atmosphere to form the catalyst.

Reactors 1, 2, and 3 are maintained at 70° C., 75° C., and 80° C. with pressures of syngas (1:1) 60 psi, 50 psi, and 40 psi, respectively. The vaporizer is operated at 120° C. for the entire run to dry the recycled catalyst to contain 1 wt % water or less. The vaporizer tails stream quickly cools to ambient temperature before it is recycled to the first reactor. The decanter is operated at ambient temperature during the entire run. The average catalyst rate is 0.87 gmole·$l^{-1}$·$hr^{-1}$ and the normal/branched aldehyde product isomer ratio is 1.37. Key operating conditions are summarized in Table 4 for an operation over 5 days.

TABLE 4

Catalyst Performance

| | |
|---|---|
| Average Rate, gmole · $l^{-1}$ · $hr^{-1}$ | 0.87 |
| Product Isomer Ratio, n/b | 1.37 |
| 1-Decene Efficiency to Aldehyde, % | 95.5 |
| Unconverted 1-Decene Efficiency, % | 2.3 |
| 1-Decene Efficiency to Isomerization, % | 2.2 |
| 1-Decene Efficiency to Decane, % | nil |

| Reactor Conditions | Reactor 1 | Reactor 2 | Reactor 3 |
|---|---|---|---|
| Rhodium, ppm | 205 | 200 | 195 |
| Ligand, wt % | 0.37 | 0.35 | 0.40 |
| Temperature, ° C. | 70 | 75 | 80 |
| Pressure, psig | 46 | 36 | 26 |
| Carbon Monoxide Partial Pressure, psi | 30 | 25 | 20 |
| Hydrogen Partial Pressure, psi | 30 | 25 | 20 |
| 1-Decene Concentration, wt % | 5.4-34 | 0.4-12 | 0.1-2.0 |
| Trans-2-Decene Concentration, wt % | 0.6-2.0 | 0.8-1.8 | 0.9-1.5 |
| Cis-2-Decene Concentration, wt % | 0.4-1.1 | 0.5-0.8 | 0.5-0.6 |
| NMP Concentration, wt % | 36-42 | 36-41 | 36-40 |
| Reaction Rate, gmole · $l^{-1}$ · $hr^{-1}$ | 1.0-2.0 | 0.5-1.1 | 0.1-0.6 |

Decanter Conditions

| | |
|---|---|
| Mixer/Degasser Temperature, ° C. | 22 |
| Mixer/Degasser Pressure, psig | 5 |
| Decanter Temperature, ° C. | 22 |
| Pressure, psig | 29 |
| Water Feed Rate, g/hr | 200-300 |
| Water in Catalyst Tails, wt % | 30-40 |
| Aldehyde in Catalyst Tails, wt % | 0.14-2.1 |
| NMP in Product Phase, wt % | 4-6 |

Extraction Column Conditions

| | |
|---|---|
| Temperature, ° C. | 45 |
| Pressure, psig | 14 |
| Agitator, strokes/min | 99 |
| Water Feed Rate, g/hr | 480 |
| Product Make Rate, g/hr | 475 |
| NMP Concentration in Product, ppm | 450 |

| Vaporizer Conditions (Unit 105) | Upper | Lower |
|---|---|---|
| Temperature, ° C. | 105 | 120 |
| Pressure, mmHg | 55 | 55 |
| Water in Tails Stream, wt % | | 0.7-1.8 |

Vaporizer Column Conditions (Unit 106)

TABLE 4-continued

| | |
|---|---|
| Head Pressure, mmHg | 55 |
| Head Temperature, °C. | 46 |
| NMP in Overhead Make, ppm | 840 |
| Base Temperature, °C. | 70 |

During the 5 day run no "alkyl-alkyl" exchange of Ligand 1A is observed in the reactors, as determined by GC chromatography and $^{31}$P NMR; in other words, no dicyclohexyl-decylphosphine is observed. The results provide evidence of improved ligand and catalyst stability, as compared with prior art ligands containing aryl-phosphorus bonds.

What is claimed is:

1. A composition comprising a class of sulfonated triorganophosphine compounds represented by the following formula:

$$\begin{array}{c} R^1 \\ | \\ P—R^3{+}(SO_3M)_n \\ | \\ R^2 \end{array}$$

wherein $R^1$ and $R^2$ each individually represent a monovalent hydrocarbyl or substituted hydrocarbyl radical selected from alkyl, aralkyl, and alicyclic radicals; wherein $R^3$ represents a divalent or polyvalent arylalkylene radical, wherein an alkyl moiety is bonded to the phosphorus atom and an aryl moiety is bonded to the alkyl moiety and is substituted with one or more sulfonate substituents; and wherein any aryl group on $R^1$ and $R^2$ and the aryl moiety on $R^3$ are each limited to only one monocyclic aryl ring; and wherein M comprises a monovalent cation, and n is an integer from 1 to 3 representing a total number of sulfonate substituents; and where in each of $R^1$ and $R^2$, the carbon atom attached to the phosphorus atom or a carbon atom bonded to the carbon atom attached to the phosphorus atom is additionally bonded to at least 2 other carbon atoms, and in $R^3$ the carbon atom attached to the phosphorus atom is bonded to at least 2 carbon atoms.

2. The composition of claim 1 wherein $R^1$ and $R^2$ are each individually selected from alkyl radicals containing from 3 to 12 carbon atoms, aralkyl radicals containing from 6 to 12 carbon atoms, and alicyclic radicals containing from 5 to 8 carbon atoms.

3. The composition of claim 1 wherein $R^1$ and $R^2$ are each individually selected from iso-propyl, iso-butyl, sec-butyl, tert-butyl, 2,2-dimethylpropyl, 2-methylbutyl, 1,1-dimethylpropyl, 2-ethylhexyl, phenylcyclohexyl, 1,2,3,4-tetrahydronaphthyl, phenylcyclopentyl, cyclopentyl, cyclohexyl, cyclooctyl, ethylcyclohexyl, norbornyl, and dicyclopentyl.

4. The composition of claim 1 wherein $R^1$ and $R^2$ are substituted with one or more substituents selected from cyano, fluoro, trifluoromethyl, trialkylsilyl, alkoxy, carboalkoxy (ester), dialkylamino, and dialkylamido.

5. The composition of claim 1 wherein $R^3$ is selected from arylalicyclic radicals having greater than 10 and less than 20 carbon atoms, and is optionally substituted with one or more substituents selected from halide, alkoxy, cyano, and/or alkyl groups.

6. The composition of claim 1 wherein $R^3$ is selected from the following radicals:

7. The composition of claim 1 selected from compounds of the following formula:

Ligand 1A

Ligand 2A
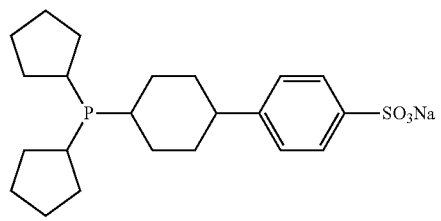
Ligand 3A
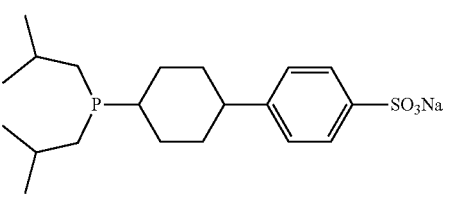
Ligand 4A
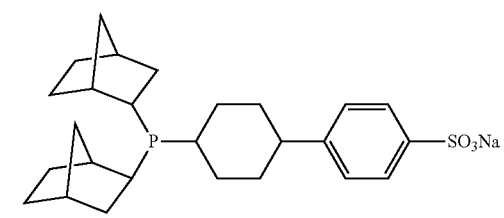
Ligand 5A
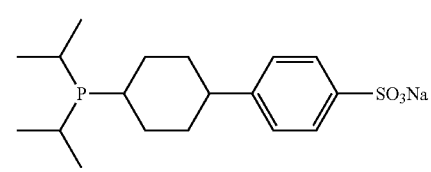
Ligand 6A
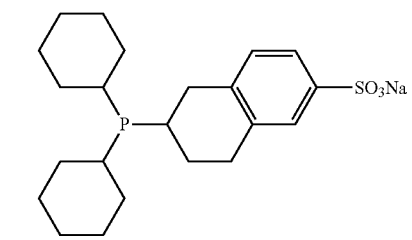
Ligand 7A
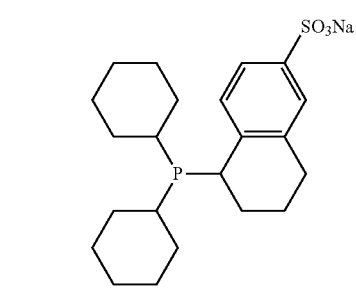
Ligand 7B
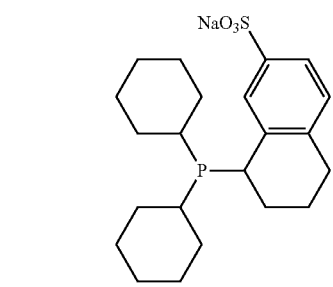
Ligand 8A
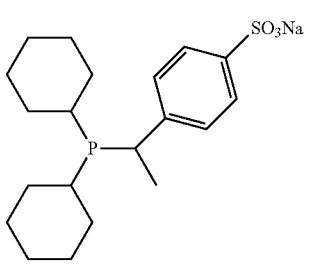
Ligand 9A
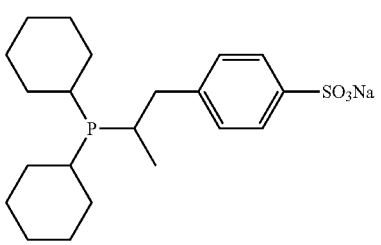
Ligand 10A
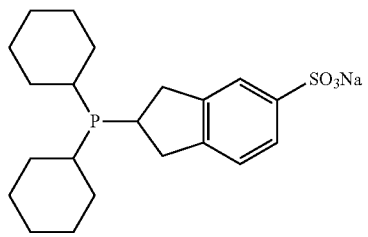
Ligand 11A
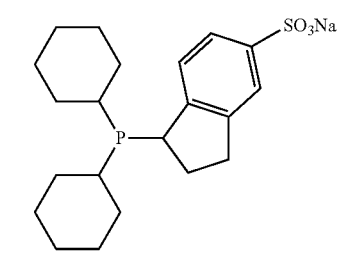
Ligand 12A
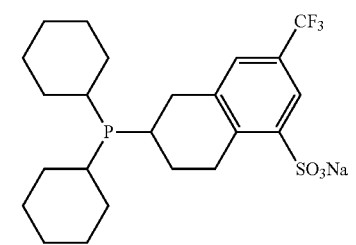
Ligand 13A
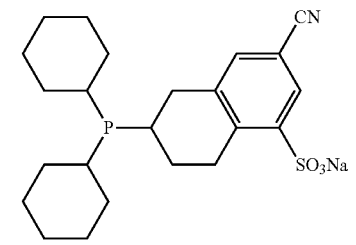

-continued

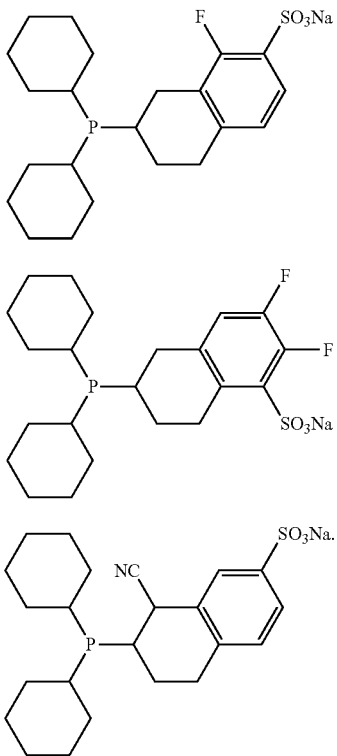

Ligand 14A

Ligand 15A

Ligand 16A

8. A complex catalyst or complex catalyst precursor composition comprising a Group 8-10 transition metal bonded to at least one ligand represented by the composition of claim 1, the transition metal optionally being further bonded to carbon monoxide, hydrogen, or both carbon monoxide and hydrogen.

9. The complex catalyst of claim 8 wherein the transition metal is selected from ruthenium, rhodium, cobalt, and iridium.

10. A complex catalyst solution or complex catalyst precursor solution comprising a solvent, a complex catalyst or catalyst precursor composition comprising a Group 8-10 transition metal bonded to at least one ligand, the solution optionally further comprising free ligand; wherein the bonded and free ligands are represented by the composition of claim 1; and wherein optionally the Group 8-10 transition metal may be further bonded to carbon monoxide, hydrogen, or both carbon monoxide and hydrogen.

11. A hydroformylation process comprising contacting one or more olefinically-unsaturated compounds with carbon monoxide and hydrogen in the presence of a transition metal-ligand complex catalyst, and optionally free ligand, wherein the ligand is represented by the composition of claim 1, the contacting being conducted under process conditions sufficient to prepare one or more corresponding aldehyde products.

12. The process of claim 11 wherein the olefin is selected from olefinically-unsaturated aliphatic hydrocarbons having from 6 to 60 carbon atoms, preferably, 10 to 50 carbon atoms.

13. The process of claim 11 wherein the olefin is selected from the group consisting of alpha olefins, internal olefins, alkyl alkenoates, alkenyl alkanoates, alkenyl alkyl ethers, alkenols, olefinically-unsaturated fatty acids, and olefinically-unsaturated fatty acid esters.

14. The process of claim 11 wherein the Group 8-10 transition metal is present in a concentration greater than 0 parts per million (ppm) and less than 1,000 ppm by weight, calculated as free metal.

15. The process of claim 11 wherein temperature is greater than 30° C. and less than 150° C.

16. The process of claim 11 wherein the total gas pressure of hydrogen, carbon monoxide, and olefinic unsaturated reactant in the hydroformylation process ranges from greater than 1 psia (7 kPa) to less than 10,000 psia (68,948 kPa).

17. The process of claim 11 wherein partial pressure of carbon monoxide is greater than 1 psia (7 kPa) and less than 1000 psia (6,8948 kPa), and wherein partial pressure of hydrogen is greater than 5 psia (35 psia) and less than 1000 psia (6,8948 kPa).

18. The process of claim 11 wherein a molar ratio $H_2$/CO of gaseous hydrogen to carbon monoxide is greater than 1/10 and less than 100/1.

19. The process of claim 11 wherein the transition metal is selected from ruthenium, rhodium, cobalt, and iridium.

* * * * *